(12) United States Patent
Li et al.

(10) Patent No.: US 6,569,451 B1
(45) Date of Patent: May 27, 2003

(54) TARGETED POLYMERIZED LIPOSOME DIAGNOSTIC AND TREATMENT AGENTS

(75) Inventors: King Chuen Li, Bethesda, MD (US); Mark David Bednarski, Los Altos, CA (US); Richard Wood Storrs, San Diego, CA (US); Henry Y. Li, Visalia, CA (US); Francois Daniel Tropper, Toronto (CA); Curtis Kang Hoon Song, Sunnyvale, CA (US); Dorothy Anna Sipkins, Palo Alto, CA (US); Jeremy Kenji Kuniyoshi, Cupertino, CA (US)

(73) Assignee: Targesome, Inc., Palo Alto, CA (US)

( * ) Notice: Subject to any disclaimer, the term of this patent is extended or adjusted under 35 U.S.C. 154(b) by 0 days.

(21) Appl. No.: 10/083,422

(22) Filed: Feb. 26, 2002

Related U.S. Application Data

(63) Continuation of application No. 09/650,276, filed on Aug. 29, 2000, now Pat. No. 6,350,466, which is a continuation of application No. 08/629,056, filed on Apr. 8, 1996, now Pat. No. 6,132,764, which is a continuation-in-part of application No. 08/286,555, filed on Aug. 5, 1994, now Pat. No. 5,512,294.

(51) Int. Cl.[7] ............... A61K 9/127; C07F 9/10; C07F 3/00
(52) U.S. Cl. .............. 424/450; 424/1.21; 424/9.321; 424/9.51; 424/600; 424/617; 554/71; 554/79
(58) Field of Search ............... 424/450, 1.21, 424/9.321, 9.51, 417, 94.3; 436/829; 424/600, 617; 554/71, 79

(56) References Cited

U.S. PATENT DOCUMENTS

| | | |
|---|---|---|
| 4,259,313 A | 3/1981 | Frank et al. |
| 4,544,545 A | 10/1985 | Ryan et al. |
| 4,784,912 A | 11/1988 | Schaeffer et al. |
| 4,801,504 A | 1/1989 | Burdick et al. |
| 4,801,722 A | 1/1989 | Hinshaw et al. |
| 4,859,777 A | 8/1989 | Toner |
| 4,938,947 A | 7/1990 | Nicolau et al. |
| 5,017,359 A | 5/1991 | Nicolau et al. |
| 5,053,443 A | 10/1991 | Sutton et al. |

(List continued on next page.)

FOREIGN PATENT DOCUMENTS

| | | |
|---|---|---|
| JP | 63054384 | 3/1988 |
| WO | 92/21017 | 11/1992 |
| WO | 97/31625 | 9/1997 |

OTHER PUBLICATIONS

Archelos et al. (1993) Ann. Neurology 34(2):145–154.

Charych et al, (1996) ChemTech 24–28.

(List continued on next page.)

*Primary Examiner*—Gollamudi S. Kishore
(74) *Attorney, Agent, or Firm*—Swanson & Bratschun, LLC

(57) ABSTRACT

Polymerized liposome particles which are linked to a targeting agent and may also be linked to a contrast enhancement agent and/or linked to or encapsulating a treatment agent. The targeting imaging enhancement polymerized liposome particles interact with biological targets holding the image enhancement agent to specific sites providing in vitro and in vivo study by magnetic resonance, radioactive, x-ray or optical imaging of the expression of molecules in cells and tissues during disease and pathology. Targeting polymerized liposomes may be linked to or encapsulate a treatment agent, such as, proteins, drugs or hormones for directed delivery to specific biological sites for treatment.

3 Claims, 25 Drawing Sheets

U.S. PATENT DOCUMENTS

| | | |
|---|---|---|
| 5,077,057 A | 12/1991 | Szoka |
| 5,078,986 A | 1/1992 | Bosworth et al. |
| 5,135,737 A | 8/1992 | Keana |
| 5,158,760 A | 10/1992 | Phillips et al. |
| 5,213,804 A | 5/1993 | Martin et al. |
| 5,246,707 A | 9/1993 | Haynes |
| 5,277,914 A | 1/1994 | Szoka |
| 5,366,881 A | 11/1994 | Singh et al. |
| 5,387,410 A | 2/1995 | Bosworth et al. |
| 5,395,619 A | 3/1995 | Zalipsky et al. |
| 5,512,294 A | 4/1996 | Li et al. |
| 5,527,528 A | 6/1996 | Allen et al. |
| 5,534,241 A | 7/1996 | Torchilin et al. |

OTHER PUBLICATIONS

Charych et al. (1993) Science 261:585–589.

Hannan (1995) Arch. Pathol Lab. Med. 119:891–893.

Hasso (1993) JRMI Special Issue: Contrast Agents 3(1):137–310 Table of Contents.

Hub et al. (1980) Angew. Chem. Int. Ed. Engl. 19:(11):938–940.

Laukkanen et al. (1994) Biochemistry 33:11664–70.

Lin et al. (1996) Bioorg. Med. Chem. Ltrs. 6(22):2755–2760.

Microparticle Immunoassay Techniques, $2^{nd}$ Ed. Seradyn, Inc., Particle Technology Division, P.O. Box 1210, Indianapolis, IN 46206 (1993).

Nagy et al., (1993) J. Cell Biochem. Supplement 17A, p. 382, Abstract CZ 403,.

Pinnaduwage and Huang (1992) Biochemistry 31(11):2850–2855.

Reichert et al. (1995) J. Am Chem. Soc. 117:829–830.

Reimer et al. (1991) Radiology 180:641–645.

Reimer et al. (1990) Radiology 177:729–734.

Reimer et al. (1992) Radiology 182:565–569.

Reisfeld et al. (1992) Laboratory Immunology II 12(2):201–216.

Sipkins et al. (1995) Radiology 197:129.

Sipkins et al. (1995) Radiology 197:276.

Spevak et al. (1996) J. Org. Chem. 61:3417–3422.

Spevak et al. (1996) J. Med. Chem. 39:1018–1020.

Spevak et al. (1995) Adv. Mater. 7(1:85–89.

Spevak et al. (1993) J. Am. Chem. Soc. 115:1146–1147.

Spevak, W., (1988) dissertation in Chemistry Dept. at University of California at Berkeley 4:110–133.

Dialog ® Abstract of Spevak, W.R, (1993) Dissertation submittal in partial satsifaction of the requirements for the degree of Doctor of Philosophy in Chemistry, Univeristy of California at Berkely.

Storrs et al. (1995) J. Am. Chem. Soc. 117(28):7301–7306.

Storrs et al. (1995) JMRI 5(6):719–724.

Unger et al. (1985) Invest. Radiol. 20:693–700.

Weissleder et al. (1990) AJR 155:1161–67.

Weissleder et al. (1991) Radiology 181:245–249.

(1991) SMRM Workshop: Contract Enhanced Magnetic Resonance, Mag. Reson. Med. 22:177–378, Table of Contents.

Unger et al. (1993) JMRI 3:195–198.

Gore et al. (1985) Magn. Reson. Imag. 3, Special Issue: Contrast Agents, Table of Contents.

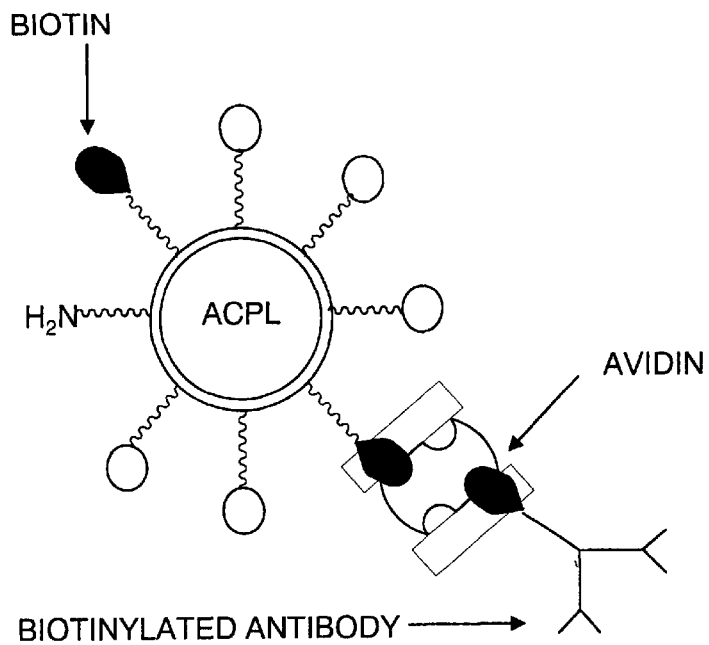
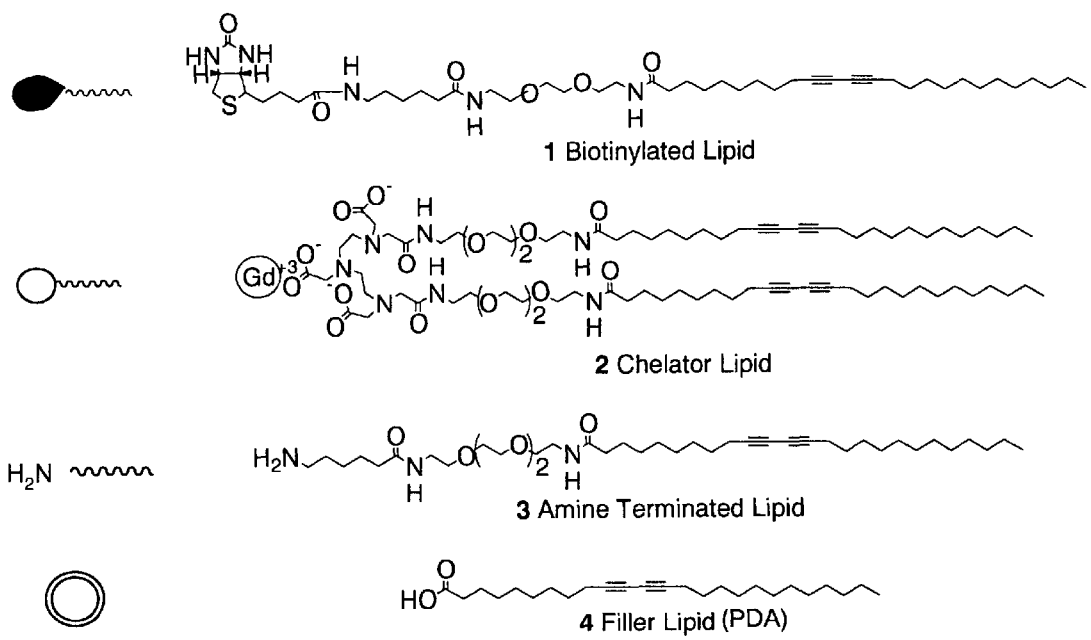
Fig. 28

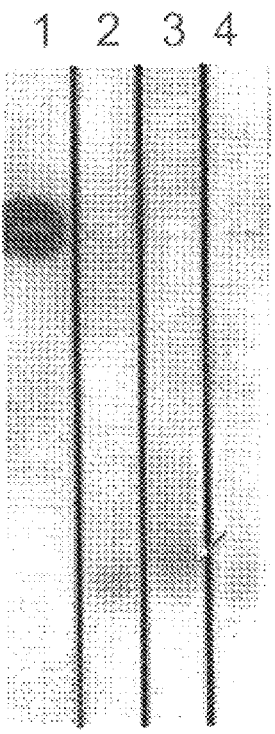 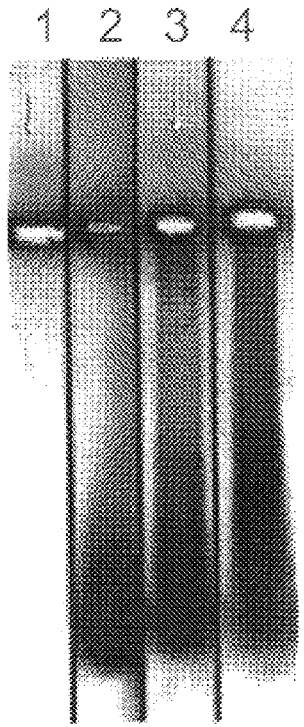
Fig. 29　　　　Fig. 30
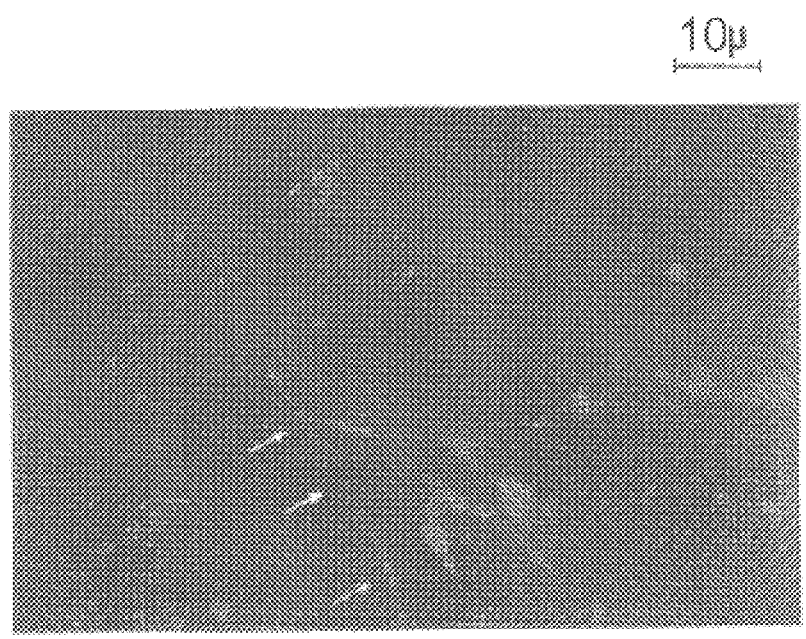
Fig. 31

TARGETED POLYMERIZED LIPOSOME DIAGNOSTIC AND TREATMENT AGENTS

CROSS REFERENCE TO RELATED APPLICATIONS

This application is a continuation of U.S. application Ser. No. 09/650,276, filed Aug. 29, 2000, entitled "Targeted Polymerized Liposome Diagnostic and Treatment Agents," now U.S. Pat. No. 6,350,466 which is a continuation of U.S. application Ser. No. 08/629,056, filed Apr. 8, 1996, entitled "Targeted Polymerized Liposome Diagnostic and Treatment Agents," now U.S. Pat. No. 6,132,764, which is a continuation-in-part of U.S. application Ser. No. 08/286,555, filed Aug. 5, 1994, entitled "Targeted Polymerized Liposome Contrast Agents," now U.S. Pat. No. 5,512,294.

BACKGROUND OF THE INVENTION

1. Field of the Invention

This invention relates to polymerized liposomes which are linked to a targeting agent and may also be linked to at least one of an image contrast enhancement agent and a therapeutic or treatment agent to provide targeted polymerized liposome diagnostic agents and targeted polymerized liposome therapeutic agents, respectively. In one embodiment, this invention relates to liposomes which may be linked to contrast ions for magnetic resonance imaging and radioisotope imaging or optical imaging by using chromophores attached to the liposome or chromophores inherent in the particle in which the polymerization adds stability in vivo. The paramagnetic or radioactive polymerized liposomes may also be linked to antibodies and ligands for specific interaction with biological targets holding the contrast agent to specific biological sites, providing in vitro and in vivo study of the expression of molecules in or on the surface of cells and tissues during disease and pathology. In another embodiment, targeted polymerized liposomes may be linked to or encapsulate a therapeutic agent, such as, for example, proteins, hormones and drugs, for directed delivery of a treatment agent to specific biological locations for localized treatment.

2. Description of Related Art

Liposomes have been used as carriers for administration of drugs and paramagnetic contrast agents. U.S. Pat. Nos. 5,077,057 and 5,277,914 teach preparation of liposome or lipidic particle suspensions having particles of a defined size, particularly lipids soluble in an aprotic solvent, for delivery of drugs having poor aqueous solubility. U. S. Pat. No. 4,544,545 teaches phospholipid liposomes having an outer layer including a modified cholesterol derivative to render the liposome more specific for a preselected organ. U. S. Pat. No. 5,213,804 teaches liposome compositions containing an entrapped agent, such as a drug, which are composed of vesicle-forming lipids and 1 to 20 mole percent of a vesicle-forming lipid derivitized with hydrophilic biocompatible polymer and sized to control its biodistribution and recirculatory half life. U.S. Pat. No. 5,246,707 teaches phospholipid coated microcrystalline particles of bio-active material to control the rate of release of entrapped water soluble biomolecules, such as proteins and polypeptides. U.S. Pat. No. 5,158,760 teaches liposome encapsulated radio-active labeled proteins, such as hemoglobin.

The use of magnetic resonance imaging contrast enhancement agents or radioactive isotopes in the body is practiced by a variety of methods. U.S. Pat. No. 5,135,737 teaches magnetic resonance imaging enhancement agents of paramagnetic metal ion chelates attached to polymers such as polyamine based molecules with antibodies attached for concentration at desired sites in the body. U.S. Pat. Nos. 4,938,947 and 5,017,359 teach an aerosol composition containing soluble fragments of bacterial wall or cell peptidoglycan which may be labeled with a paramagnetic element and encapsulated in liposomes which may be administered as an aerosol. U.S. Pat. No. 5,078,986 teaches magnetic resonance imaging agents of a chelate of a paramagnetic element carried by or within the external surface of a liposome and released at a desired organ or tissue site. PCT Publication Number WO 92/21017 teaches specific liposomes complexed with paramagnetic ions to prolong their blood pool half life and control magnetic resonance relaxivity. Liposomes as MR contrast agents has been reviewed by Unger, E. C., Shen, D. K., and Fritz, T. A., Status of Liposomes as MR Contrast Agents, JMRI, 3, 195–198, (1993).

The need for recirculation of paramagnetic contrast agents in the body, that is avoidance of rapid endocytosis by the reticuloendothelial system and avoidance of rapid filtration by the kidney, to provide sufficient concentration at a targeted site to afford necessary contrast has been recognized. The use of small molecules, such as gadolinium diethylenetriaminepentaacetic acid, is restricted due to rapid renal excretion while most liposomes, having diameters >800 nm, are quickly cleared by the reticuloendothelial system. Attempts to solve these problems have involved use of macromolecular materials, such as gadolinium diethylenetriaminepentaacetic acid derived polysaccharides, polypeptides, and proteins. These agents have not achieved the versatility in chemical modification to provide for both long recirculation times and active targeting.

Prior attempts to construct bifunctional, ligand-bearing magnetic resonance contrast agents have not been satisfactory due to insufficient sensitivity, poor target specificity and lack of characterization. Gore, J. C. and Smith, F. W., Special Issue: Contrast Agents, Magn. Reson. Img., 3, 1–97, (1985); Hasso, A. N. and Stark, D. D., Special Issue: Contrast Agents, JMRI, 3, 137–310, (1993); and Wehrli, F. W., SMRM Workshop: Contrast Enhanced Magnetic Resonance, Magn. Reson.. Med., 22, 177–378, (1991).

Receptor-directed contrast agents for MRI have been attempted using iron oxide particles, but the chemistry and characterization of the particle has been poorly defined and thus it has been difficult to achieve control over non-specific adhesion, blood pool half life and the versatility for both T1 and T2* imaging modes. In addition, no radioisotope imaging is possible using these iron-based agents which further limits their usefulness. Reimer, P., Weissleder, R., Brady, T. J., Baldwin, B. H., Tennant, B. C., and Wittenberg, J., Experimental Hepatocellular Carcinoma: MR Receptor Imaging, Radiology, 180, 641–645 (1991), Reimer, P., Weisslender, R., Lee, A. S., and Brady, T. J., Receptor Imaging: Application to MR Imaging of Liver Cancer, Radiology, 177, 729–734 (1990), Reimer, P., Weissleder, R., Wittenberg, J., and Brady, T. J., Receptor-Directed Contrast Agents for MR Imaging: Preclinical Evaluation With Affinity Assays, Radiology, 182, 565–569 (1992), and Weissleder, R., Reimer, P., Lee, A. S., Wittenberg, J. and Brady, T. J., MR Receptor Imaging: Ultrasmall Iron Oxide Particles Targeted to Asialoglycoprotein Receptors, AJR, 155, 1161–67, (1990).

Antibody MR imaging has been described by Unger, E. C., Totty, W. G., Neufeld, D. M., Otsuka, F. L., Murphy, W. A., Welch, M. S., Connett, J. M., and Philpott, G. W., Magnetic Resonance Imaging Using Gadolinium labeled Monoclonal Antibody, Invest. Radiol., 20, 693–700. (1985), and Weissleder, R., Lee, A. S., Fischman, A. J., Reimer, P., Shen, T., Wilkinson, R., Callahan, R. J., and Brady, T. J., Polyclonal Human Immunoglobulin G Labeled with polymeric Iron Oxide: Antibody MR Imaging, Radiology, 181, 245–249, (1991). In the former case, one is limited by the amount of contrast enhancement that can be achieved by direct attachment of chelator to an antibody. In the latter case, the iron oxide particle is not amenable to control over surface functionality needed to reduce non specific adhesion and the particle is not well characterized or well tolerated in vivo.

The economic driven requirement for improved in vitro diagnostic techniques for medicine is also well recognized. Hannon, Robert E., Future Practices in Diagnostic Medicine, Arch Pathol Lab Med, Vol 119, pg 890–893 (October 1995) A common technique presently used in diagnostic medicine for detection of the presence of specific antigens in solution is addition of latex beads coated with antibodies to the solution and detection of micro-agglutinated products, as described in Microparticle Immunoassay Techniches, 2nd Ed., Seradyn, Inc., Particle Technology Division, P.O. Box 1210, Indianapolis, Ind. 46206 (1993) and U.S. Pat. Nos. 4,801,504 and 5,053,443. However, detection of micro-agglutinated products, approximately 1 $\mu$m in size, is very difficult.

Currently used in vitro enzyme linked immunoassays (ELISA) have a sensitivity in the order of 1 picomolar concentration (0.5 $\mu$g/10 mL). Other in vitro assay technologies, including radioactive immunoassay systems, have sensitivities 2 to 3 orders of magnitude more sensitive than ELISA assays. While polymerase chain reaction (PCR) based technologies have the technology is limited to detection of nucleic acids.

The expression of glycoproteins on a cell surface is currently detected using assays requiring multiple steps and frequently resulting in low sensitivity. For example, for assays of protein expression on activated endothelial cells, a first step involves the use of an antibody against the cell surface protein followed by multiple steps to amplify the ability for detection of the resulting complexes using flourescent techniques, such as, for example, fluorescent antivated cell flow cytometry, fluorescent antivated cell sorting, and fluorescent microscopy.

It has been recognized that unique proteins called cell adhesion molecules (CAMs) are expressed by endothelial cells during a variety of physiological and disease processes. Reisfeld, R. A., Monoclonal Antibodies in Cancer Immunotherapy, Laboratory Immunology II, Vol. 12, No. 2, pgs. 201–216, (June 1992) and Archelos, J. J., Jung, S., Maurer, M., Schmied, M., Lassmann, H., Tamatani, T., Miyasaka, M., Toyka, K. V. and Hartung, H. P., Inhibition of Experimental Autoimmune Encephalomylitis by the Antibody to the Intercelluler Adhesion Molecule ICAM-1, Ann. of Neurology, Vol. 34, No. 2, pgs. 145–154 (1993) Multiple endothelial ligands and receptors, including CAMs, are known to be upregulated during various pathologies, such as inflammation and neoplasia. Currently, the evaluation of the pathophysiology of the cell adhesion molecules is generally limited to in vitro assays.

SUMMARY OF THE INVENTION

This invention, in one embodiment, relates to nanoscale polymerized liposome particles based upon lipids having a polymerizable functional group and a metal chelator to attach an imaging enhancement agent, such as paramagnetic or radioactive ions, which assemble to form imaging enhancement polymerized liposomes. In preferred embodiments, the imaging enhancement polymerized liposomes are derivatized with antibodies and/or ligands for in vivo binding to cell surface receptors of targeted cells. In particular, these receptors can be located on the endothelium which eliminates the need for distribution of the active agent out of the blood pool. Paramagnetic polymerized liposomes according to this invention have been found to be well tolerated by rabbits, mice and rats, even on repeated administration, and effectively recirculate in the bloodstream, avoiding rapid endocytosis by the reticuloendothelial system. These materials provide good magnetic resonance imaging signal enhancement of targeted cells, liver and kidney, for long periods of time, of 90 minutes and more.

The polymerized liposomes of this invention are stable in vivo and provide for effective control of particle size, surface functionality, active ion density and water accessibility to maximize their effective relaxivity for T1 and T2* magnetic resonance imaging enhancement of specific biological systems. For example, the polymerized liposomes of this invention may have a plurality of metal ions for high relaxivity per particle providing highly effective magnetic resonance imaging enhancement and may also have attached antibodies or ligands specific for cellular receptors, resulting in a sensitive probe for areas of vascular tissue expressing these cell surface molecules. Receptors of protein adhesins on the endothelium surface are of particular interest in this targeting scheme because they are expressed extensively during pathological processes of inflammation for the recruitment of leukocytes or in the process of angiogenesis for vascularization of diseased tissue, such as tumors. Targeted polymerized liposomes provide for in vivo magnetic resonance imaging histology that enables early evaluation of changes in the endothelium in disease processes due to the attachment of a high concentration of paramagnetic or superparamagnetic ions to specific receptors on specifically targeted tissue or endothelium of concern.

This invention provides various methods for in vitro assays. For example, antibody-conjugated polymerized liposomes, according to this invention, provide an ultra-sensitive diagnostic assay for specific antigens in solution. Polymerized liposomes of this invention having a chelator head group chelated to spectroscopically distinct ions provide high sensitivity for enzyme linked immunoassays. Polymerized liposomes of this invention having a fluorophore head group provide a method for detection of glycoproteins on cell surfaces.

In one embodiment of this invention, a targeting polymerized liposome particle comprises: an assembly of a plurality of liposome forming lipids each having an active hydrophilic head group linked by a bifunctional linker portion to the liposome forming lipid, and a hydrophobic tail group having a polymerizable functional group polymerized with a polymerizable functional group of an adjacent hydrophobic tail group of one of the plurality of liposome forming lipids, at least a portion of the hydrophilic head groups having an attached targeting active agent for attachment to a specific biological molecule. In another embodiment, the targeting polymerized liposome particle has a second portion of the hydrophilic head groups with functional surface groups attached to an image contrast enhancement agent to form a targeting image enhancing polymerized liposome particle. In yet another embodiment, a portion of the hydrophilic head groups have functional surface groups attached to or encapsulating a treatment agent for interaction with a biological site at or near the specific biological molecule to which the particle attaches, forming a targeting delivery polymerized liposome particle or a targeting image enhancing delivery polymerized liposome particle.

This invention provides a method of assaying abnormal pathology in vitro comprising, introducing a plurality of targeting polymerized liposome particles targeted to a molecule involved in the abnormal pathology into a fluid contacting the abnormal pathology, the targeting polymerized liposome particles attaching to a molecule involved in the abnormal pathology, and detecting in vitro the targeting polymerized liposome particles attached to molecules involved in the abnormal pathology.

This invention also provides a method of diagnosing abnormal pathology in vivo comprising, introducing a plurality of targeting image enhancing polymerized particles targeted to a molecule involved in the abnormal pathology into a bodily fluid contacting the abnormal pathology, the targeting image enhancing polymerized particles attaching to a molecule involved in the abnormal pathology, and imaging in vivo the targeting image enhancing polymerized particles attached to molecules involved in the abnormal pathology.

This invention further provides a method of therapeutic treatment comprising, introducing into a bodily fluid contacting an area of desired treatment a plurality of targeting delivery polymerized liposome particles targeted to a molecule at or near the site of desired treatment and having a desired therapeutic agent attached or encapsulated, the targeting delivery polymerized liposome particles attaching to molecules at or near the site of desired treatment rendering the therapeutic agent available at the site of desired treatment.

Further details of preparation and use of the targeting paramagnetic polymerized liposomes of this invention in magnetic resonance imaging is described in: Storrs, R. W., Tropper, F. D., Li, H. Y., Song, C. K., Kuniyoshi, J. K., Sipkins, D. A., Li, K. C. P. and Bednarski, M. D., Paramagnetic Polymerized Liposomes: Synthesis, Characterization, and Applications for Magnetic Resonance Imaging, J. Am. Chem. Soc., Vol. 117, No. 28, pgs. 7301–7306, (August 1995) and Storrs, R. W., Tropper, F. D., Li, H. Y., Song, C. K., Sipkins, D. A., Kuniyoshi, J. K., Bednarski, M. D., Strauss, H. W. and Li, K. C. P., Paramagnetic Polymerized Liposomes as New Recirculating MR Contrast Agents, JMRI, Vol. 5, No. 6, pgs.719–724, (November/December 1995), which publications are incorporated herein by reference in their entireties.

BRIEF DESCRIPTION OF THE DRAWINGS

The invention will be described in detail with reference to the drawings wherein:

FIG. 28 is a schematic showing of an antibody-conjugated paramagnetic polymerized liposome as prepared in Example VIII;

FIG. 29 is a photograph in color of gel electrophoresis using anti-avidin alkaline phosphatase as described in Example IX;

FIG. 30 is a photograph in color of gel electrophoresis using anti-IgG alkaline phosphatase as described in Example IX;

FIG. 31 is a fluorescence micrograph in color showing cell binding of fluorescent antibody-conjugated paramagnetic polymerized liposomes as described in Example X;

DESCRIPTION OF PREFERRED EMBODIMENTS

Figure 3:
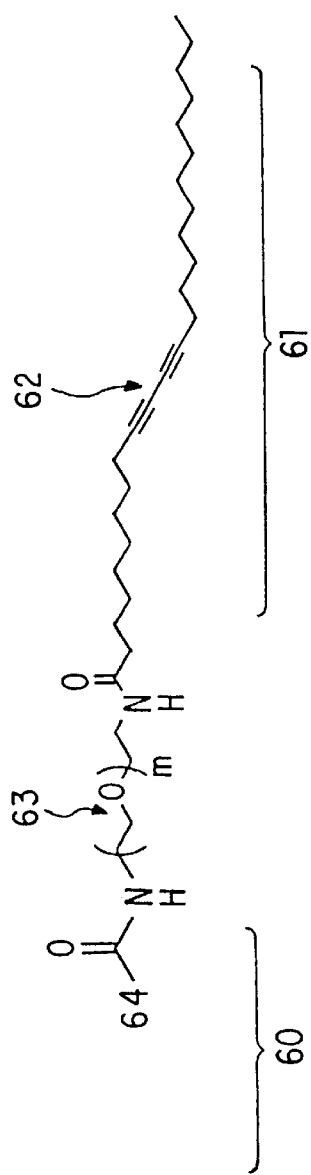
FIGS. 2 and 3 schematically show polymerizable lipid molecules according to one embodiment of this invention.

The polymerized liposomes of this invention are self-assembled aggregates of lipid molecules which offer great versatility in particle size and surface chemistry. The size of the polymerized liposomes can be controlled by extrusion. The polymerized liposomes can be a mixture of lipids which provide different functional groups on the hydrophilic exposed surface. For example, some hydrophilic head groups can have functional surface groups, for example, biotin, amines, cyano, carboxylic acids, isothiocyanates, thiols, disulfides, α-halocarbonyl compounds, α, β-unsaturated carbonyl compounds and alkyl hydrazines for attachment of targeting active agents, such as antibodies, ligands, proteins, peptides, carbohydrates, vitamins, drugs, and combinations of these materials to form antigenic determinants for specific targeting and attachment to desired cell surface molecules. Other such head groups may have an attached or encapsulated treatment agent, such as, for example, antibodies, hormones and drugs for interaction with a biological site at or near the specific biological molecule to which the polymerized liposome particle attaches. Other hydrophilic head groups can have a functional surface group of diethylenetriamine pentaacetic acid, ethylenedinitrile tetraacetic acid, tetraazlocyclododecane 1,4,7,10-tetraacetic acid, porphoryin chelate and cyclohexane-1,2,-diamino-N,N'-diacetate for attachment to an image contrast enhancement agent, such as, specifically, a lanthanide-diethylenetriamine pentaacetic acid chelate for coupling a metal which provides for the paramagnetism and magnetic resonance contrast properties or for chelation of radioactive isotopes or other imaging materials.

These lipids can be combined in varied proportions to produce image enhancing paramagnetic or radioactive polymerized liposomes with a broad spectrum of chemical and biological properties. The magnetic resonance imaging R1 and R2* relaxivities can be controlled by the nature of the metal chelate and the distance of the metal from the surface of the particle. The hydrophobic tail groups of the lipids are derivatized with polymerizable groups, such as diacetylene groups, which irreversibly cross-link, or polymerize, when exposed to ultraviolet light or other radical, anionic or cationic, initiating species, while maintaining the distribution of functional groups at the surface of the liposome. The resulting polymerized liposome particle is stabilized against fusion with cell membranes or other liposomes and stabilized towards enzymatic degradation. In this manner, many thousands of active lanthanide ions or radioisotopes may be attached to one particle that may also bear several to hundreds of ligands for in vivo adherence to targeted surfaces. For T1 contrast agents the polymerized liposomes suitably have about 7 to about 30 percent metal chelating lipids, while for T2* contrast agents the polymerized liposomes have about 50 to about 99 percent metal chelating lipids. The large number of lanthanide ions renders the paramagnetic polymerized liposomes of this invention very sensitive magnetic resonance contrast agents with high R1 and R2* molar relaxivities and high ion concentration while the multiple ligand binding sites improves in vivo binding affinity and specificity. This improved binding can also be utilized therapeutically to block cell adhesion to endothelial receptors in vivo. Blocking these receptors can be useful to control pathological processes, such as inflamation and control of metastatic cancer. For example, multi-valent sialyl Lewis X derivatized liposomes can be used to block neutrophil binding and antibodies against VCAM-1 on polymerized liposomes can be used to block lymphocyte binding, for example T-cells.

Figure 1:
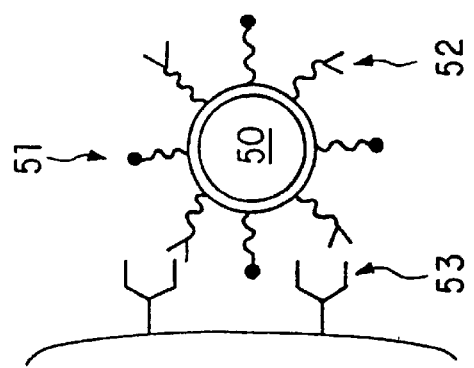
FIG. 1 schematically shows the action of targeted paramagnetic polymerized liposomes according to this invention.

FIG. 1 schematically shows the action of the polymerized liposome contrast agents of this invention. Polymerized liposome contrast agent core 50 has attached to its exterior surface contrast ions 51 for imaging enhancement, such as $Gd^{3+}$ for T1 MRI agents, $Dy^{3+}$ for T2* MRI agents and Tc or In ions for radioisotope imaging, and targeting groups 52, such as antibodies and ligands, tailored for attachment to cell surface molecules 53, such as receptors, ligands and antigenic determinants.

Suitable image enhancing polymerized liposomes for use in this invention are those in which a contrast agent, paramagnetic ion or radioisotope, is provided at the surface of the particle. Preferably, the particle also contains groups to control nonspecific adhesion and reticuloendothelial system uptake with an agent to target the particle to areas of pathology related to changes in the endothelium, providing identification of changes in the endothelium during disease and to sequester the liposome in these areas without the need for the particle to leave the circulatory system. The polymerized liposomes of this invention provide: controlled surface functionality and particle rigidity to prolong blood pool half life and retain the particle in the circulatory system, as desired; a targeting group, such as a ligand or antibody, to direct the particle to the desired region of interest; and a contrast enhancement material, such as a paramagnetic ion for MRI, a radioisotope, such as Tc or In, for radioisotope imaging, or a heavy metal, such as lead or barium, for standard x-ray analysis or a chromophore for optical imaging, to detect the presence of the particles in vivo.

The component lipids of the polymerized liposomes of this invention may be purified and characterized individually using standard, known techniques and then combined in controlled fashion to produce the final particle. The polymerized liposomes of this invention can be constructed to mimic native cell membranes or present functionality, such as ethylene glycol derivatives, that can reduce their potential immunogenicity. Additionally, the polymerized liposomes of this invention have a well defined bilayer structure that can be characterized by known physical techniques such as transmission electron microscopy and atomic force microscopy.

Figure 2:
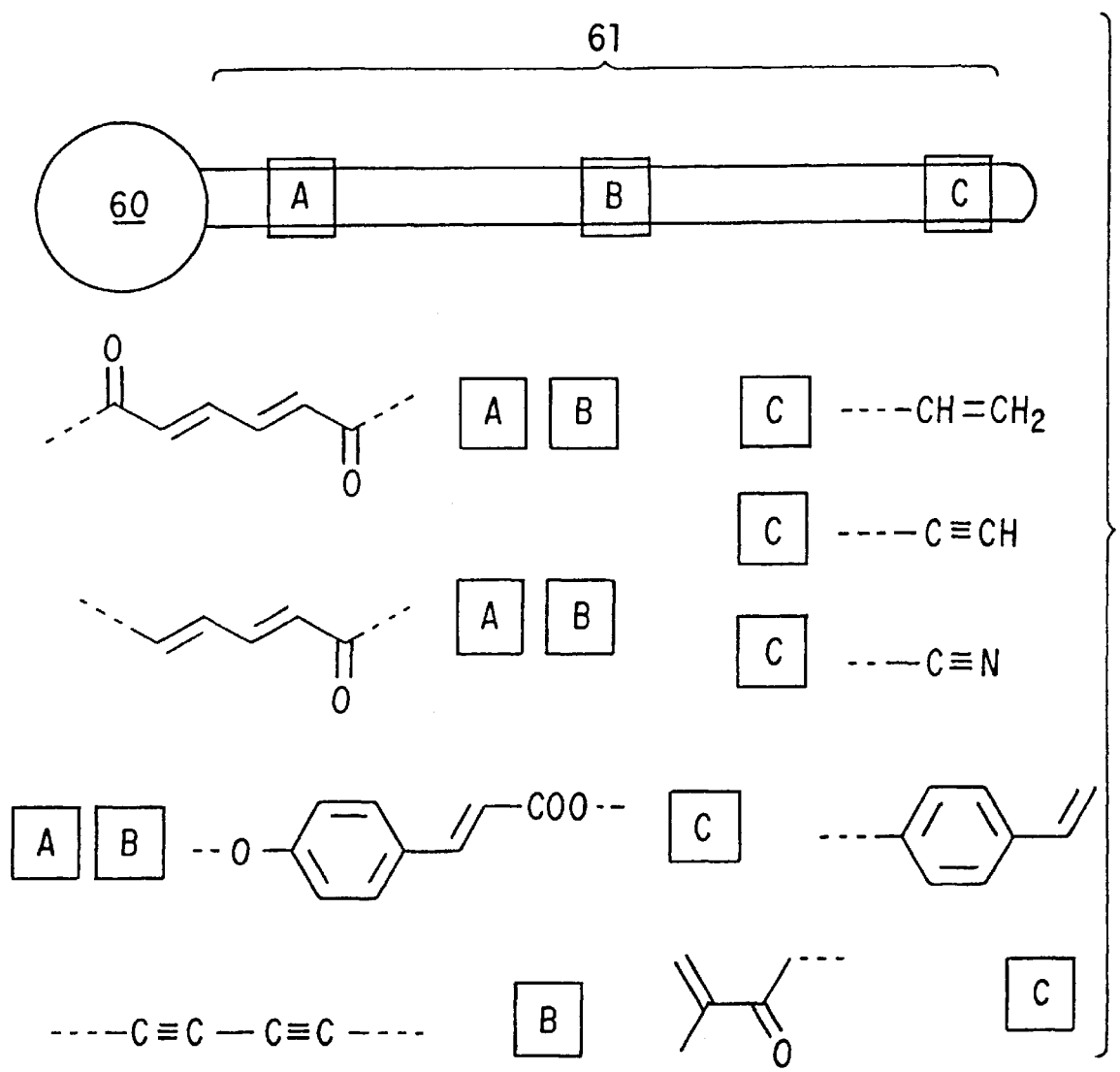

FIGS. 2 and 3 schematically show a polymerizable lipid molecule for use in this invention. The amphiphilic lipid molecule has a polar head group 60 and a hydrophobic tail group 61. The tail portion of the lipid has a polymerizable functional group 62, such as diacetylene, olefins, acetylenes, nitriles, alkyl styrenes, esters, thiols, amides and α, β unsaturated carbonyl compounds forming liposomes that will polymerize upon irradiation an electromagnetic source, such as, with UV light or by chemical or thermal means. FIG. 2 shows polymerizable functional groups which may be located at specific positions A, B and C on tail group 61. As shown in FIG. 3, the head group and tail group are joined by variable length linker portion 63. The length of the linker portion, indicated by m, controls the distance of the active agent from the surface of the particle to make it more available for its active function. The linker portion may be a bifunctional aliphatic compounds which can include heteroatoms or bifunctional aromatic compounds. Preferred linker portions are compounds such as, for example, variable length polyethylene glycol, polypropylene glycol, polyglycine, bifunctional aliphatic compounds, for example amino caproic acid, or bifunctional aromatic compounds. The head group has a functional surface group 64, such as diethylenetriamine pentaacetic acid (DPTA), ethylenedinitrile tetraacetic acid (EDTA), tetraazocyclododecane 1,4,7, 10-tetraacetic acid (DOTA), cyclohexane-1,2- diamino-N, N'-diacetate (CHTA) for chelating a paramagnetic or radioactive intensifying agent for contrast enhancement, or biotin, amines, carboxylic acids and alkyl hydrazines for coupling biologically active targeting agents, such as ligands, antibodies, peptides or carbohydrates for specific cell surface receptors or antigenic determinants.

Generally, the lipids suitable for use in this invention have: an active head group, for at least one of targeting, image contrast enhancement and/or for treatment, a linker portion for accessibility of the active head group; a hydrophobic tail for self-assembly into liposomes; and a polymerizable group to stabilize the liposomes.

Figure 4:
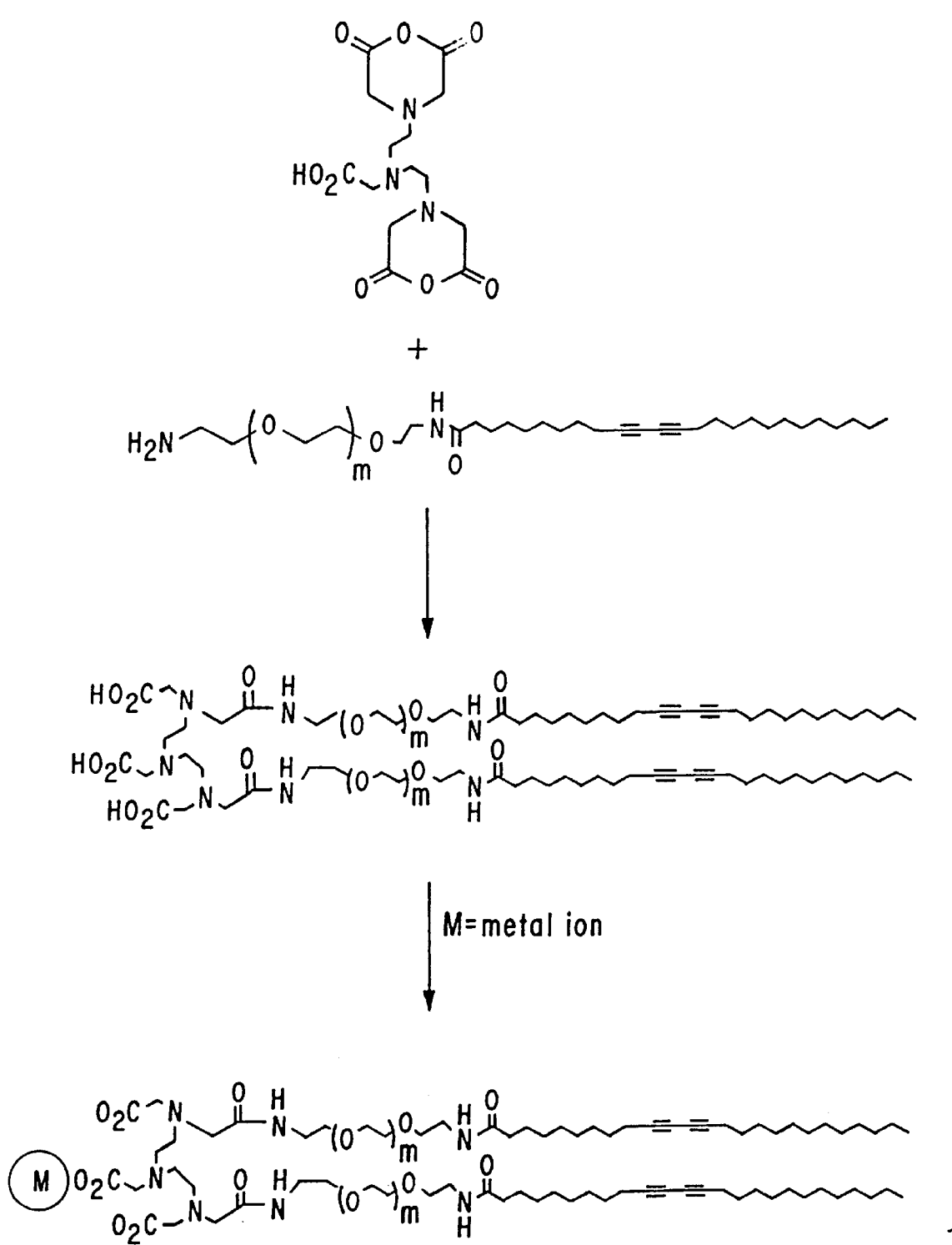
FIG. 4 shows the synthesis of a metal chelated lipid according to one embodiment of this invention.

A unique lipid is synthesized containing pentacosadiynoic acid conjugated to diethylenetriamine pentaacetic acid via a variable length polyethylene glycol linker as shown in FIG. 4. These amphipathic molecules have metal chelates as head groups connected to a lipid tail which contains a polymerizable diacetylene moiety. The linker length can be controlled by the choice of commercially available variable length polyethylene glycol derivatives.

Figure 5:
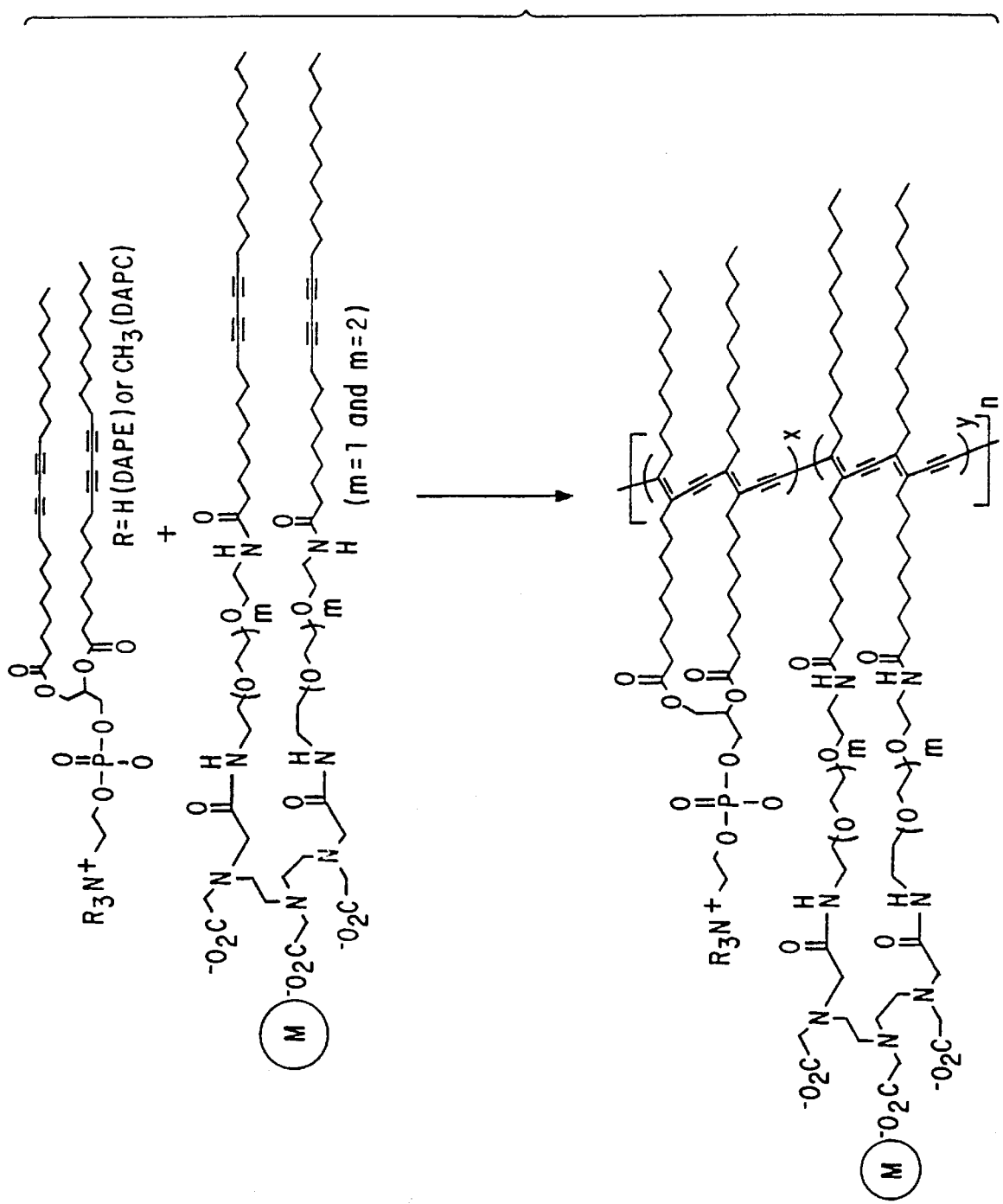
FIGS. 5 and 6 show formation of paramagnetic polymerized liposomes from the metal chelated lipid shown in FIG. 4 with filler lipids DAPC, DAPE or PDA according to one embodiment of this invention.

Specifically, we have synthesized compounds, such as shown in FIG. 4, by reacting the NHS ester of the lipid pentacosadiynoic acid (PDA) with triethyleneglycol-diamine and tetraethyleneglycol-diamine linkers to form the corresponding $PEG_m$-PDA amides, m=1 or 2, then reacting the $PEG_m$-PDA amide with diethylenetriamine pentaacetic acid dianhydride (DTPAA) to form diethylenetriamine pentaacetic acid-bis(tri or tetraethylene glycol-pentacosadiynoic acid) diamide (DTPA-bis-($PEG_m$-PDA), m=1 or 2 diamide). The diamide is then treated with a metal ion source M, such as gadolinium trichloride, dysprosium trichloride or a technicium or indium derivative to form the amphiphilic metal chelate as shown in FIG. 4 with a polyethylene linker (m=1 and m=2). The diamide-lanthanide chelate, shown in FIG. 4 and as a reactant in FIG. 5, is mixed with a matrix lipid of diacetylenic choline (DAPC, R=CH$_3$) or diacetylinic ethanolamine (R=H), shown in FIG. 5, pentacosadiynoic acid (PDA) or derivatives of PDA in an amount to result in the desired surface density of contrast agent on the polymerized liposomes. The matrix lipid forms polymerizable liposomes under a variety of conditions and closely mimics the topology of in vivo cell membranes.

Figure 6:
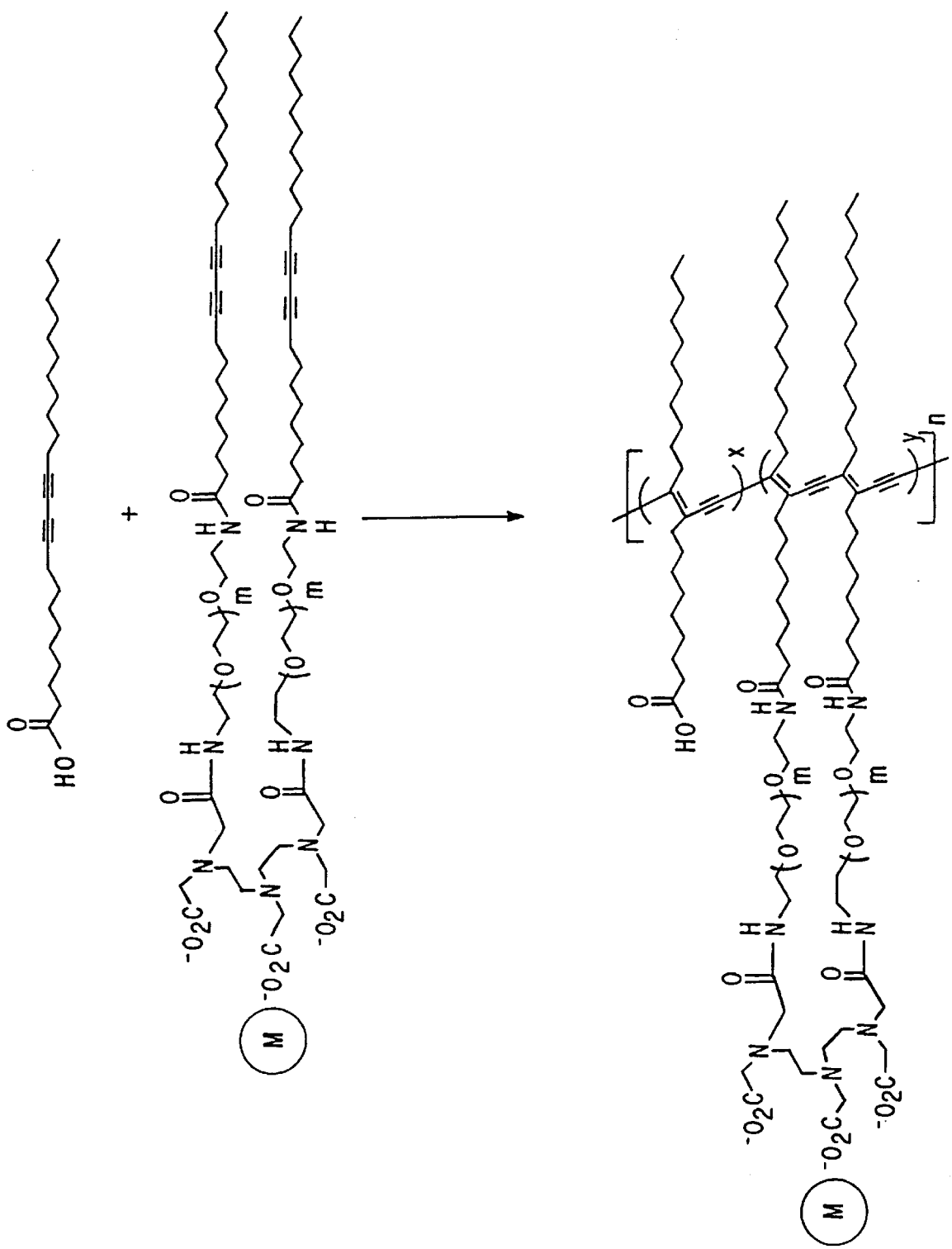

To form the paramagnetic polymerized liposome shown as the product in FIGS. 5 and 6, the metal chelated diamide shown in FIG. 4 is doped into the DAPC, as shown in FIG. 5, or PDA, as shown in FIG. 6, matrix in organic solvent. The organic solvent is evaporated and the dried lipid film is hydrated to a known lipid density, such as 15 mM total lipid, with the desired buffer or water. The resulting suspension is sonicated at temperatures above the gel-liquid crystal phase transition for DAPC or PDA, $T_m \approx 40°$ C., with a probe-tip sonicator. A nearly clear, colorless solution of emulsified vesicles, or liposomes, is produced. We have determined by transmission electron microscopy and atomic force microscopy that these liposomes are on average 30 to 200 nm in diameter. Their size can be reduced by extrusion at temperatures greater than $T_m$ through polycarbonate filters with well defined porosity. The liposomes are polymerized by cooling the solution to 4° C. on a bed of ice and irradiating at 254 nm with a UV lamp. Alternatively, the liposomes can be irradiated at room temperature and then cooled while continuing UV irradiation. The resulting paramagnetic polymerized liposomes, diagramatically shown as the products in FIGS. 5 and 6, are orange in color when using DAPC with two visible absorption bands centered at 490 nm and 510 nm arising from the conjugated ene-yne diacetylene polymer and generally blue in color when using PDA with absorption bands around 540 nm and 630 nm. These liposomes can undergo a blue to red transition when molecules bind to their surface after heating or resonication or after standing at room temperature for extended times or being treated with organic solvents. This transition may be useful for developing a detection system for these conditions.

We have constructed paramagnetic polymerized liposomes using the above techniques with 2.5 to 100 mol % of the gadolinium chelated diamide shown in FIG. 4, with the polyethylene glycol linker m=1 and m=2, and sizes ranging from 30 nm to 200 nm in diameter. We have determined the maximum T1 relaxivity, showing the best contrast, is obtained with 15% gadolinium chelated diamide and 85% DAPC with m=2 and having 200 nm particle size. High relaxivity is also observed with 30% gadolinium chelated diamide and 70% PDA with m=1 and having a variable particle size of about 10 to about 200 nm. Results of a variety of these measurements using DAPC matrix lipid are shown in Tables 1 and 2.

TABLE 1

| Gadolinium-diamide (%) | Size (nm) | R1 ($s^{-1}mM^{-1}$) | R2 ($s^{-1}mM^{-1}$) |
|---|---|---|---|
| 5.7 (m = 1) | 200 | 5.7 | Not Det. |
| 5.7 (m = 2) | 200 | 8.3 | Not Det. |
| 10 (m = 2) | 200 | 9.2 | Not Det. |
| 15 (m = 2) | 200 | 14.6 | Not Det. |
| 20 (m = 2) | 200 | 8.9 | Not Det. |
| 30 (m = 2) | 200 | 7.7 | Not Det. |
| 10 (m = 2) | 100 | 10.9 | 16.0 |
| 10 (m = 2) | 80 | 9.6 | Not Det. |
| 10 (m = 2) | 50 | 8.6 | 18.3 |
| 10 (m = 2) | 30 | 7.8 | 19.2 |
| Gd (DTPA) Magnevist, Lab., Wayne N.J. | | 4.4 | 1.9 Berle |

To demonstrate the dependence on linker length, it is seen from Table 1 that when m=2 (R1=8.3) the metal ion appears to be suspended off the surface of the polymerized liposome allowing greater aqueous accessibility and hence greater relaxation than when m=1 (R1=5.7).

Similar measurements were made using PDA liposomes as the matrix lipid and the gadolinium chelated diamide (m=1). The results are shown in Table 2.

TABLE 2

| Gadolinium-diamide (%) | R1 ($s^{-1}mM^{-1}$) |
|---|---|
| 10 | 8.86 |
| 30 | 8.67 |
| 50 | 4.34 |
| 50* | 4.19 |
| 100 | 3.4 |

*1% biotin-DAPE

It is seen from Table 2 that liposome formulations of 10% and 30% metal chelator diamide and 90% and 70% PDA, respectively, exhibited the highest relaxivity of over 8 $mM^{-1}sec^{-1}$, while formulations of 50, and 100% metal chelator diamide had lower relaxivities. It is desired that the paramagnetic polymerized liposomes of this invention have a long half life in the recirculating blood pool to find their desired targeted receptors in vivo. To aid in retention in the blood pool, the overall size of the paramagnetic polymerized liposomes can be controlled by extrusion to reduce elimination from the blood pool by the reticuloenthelial system. Additionally, the surface chemistry of the polymerized liposomes can be modified to evade the hepatic and immune systems, for example, liposomes derivatized with polyethylene glycol decrease the rate of elimination by the reticuloendothelial system. Particle rigidity can also be controlled by the polymerization time and method which modifies recirculation time.

In a similar manner as described above with respect to FIGS. 5 and 6, dysprosium chelated lipids may be used to construct T2* untargeted or targeted paramagnetic polymerized liposomes according to this invention. Dysprosium is a desirable metal for T2* contrast since its magnetic susceptibility is the largest of any element and it is easily incorporated into a diethylenetriamine pentaacetic acid chelate. It may not be desired to use a matrix lipid to separate the paramagnetic metal centers, as found desirable for Ti paramagnetic polymerized liposomes. The chelator lipid described in FIG. 4 can be treated with dysprosium trichloride in sodium bicarbonate to produce the Dy-diacetylene lipid having $M=Dy^{+3}$ in FIG. 4. Single component paramagnetic polymerized liposomes can be constructed from these compounds by sonication, extrusion and polymerization in the manner described above, as shown in FIG. 6, with x=0. Alternatively, the dysprosium lipid reactant can be doped into DAPC, DAPE or PDA lipids at varying percentages.

For transmission electron microscopy (TEM), a polymerized liposome dispersion was deposited by freeze-drying onto the sample grid of the microscope and stained with osmium tetraoxide for 15 minutes. The micrograph shown as FIG. 7 was taken at a magnification of 21000 times and shows the polymerized liposome particles as ellipsoids having diameters of about 50 to 200 nm.

For Atomic Force Microscopy (AFM), samples were prepared by covering freshly cleaved mica with a solution of paramagnetic polymerized liposomes, 15 mM total lipid, for 1 to 2 minutes. The solution was recovered by pipet and the mica surface rinsed with a stream of distilled water. AFM images were obtained on an Explorer Life Sciences model 200 (Topometrix, Santa Clara, Calif.). The AFM was operated in the contact mode using the minimum force necessary to prevent hopping of the cantilever tip. The raw images were flattened either line-by-line or through a user-defined baseline plane, as appropriate, using software supplied by Topometrix. The paramagnetic polymerized liposomes, as shown in the AFM micrograph of FIG. 8, were readily observed as flattened ellipsoids with in-plane dimension similar to the 50 to 200 nm in diameter obtained by transmission electron microscopy (TEM). With non-extruded paramagnetic polymerized liposomes, smaller particles were more abundant than observed by TEM due to the higher resolution of AFM relative to TEM. The AFM provides more accurate sampling of particle sizes than TEM due to its higher resolution. Confidence in the uniformity of sampling particle sizes using AFM is enhanced since forward and reverse scanned images appeared identical within the resolution of the technique. We have found that AFM provides a simple and reliable method to assay particle sizes of the paramagnetic polymerized liposomes of this invention.

We have found that the metal chelate lipid, such as DTPA, is necessary to obtain images when mounting the sample on cleaved mica. Polymerized lipids lacking the metal chelate lipid did not produce AFM images using the above-described method. It is believed that the metal chelate lipid serves as a unique functionality for attachment of these materials to the mica, probably by chelating DTPA to metals on the cleaved mica. The metal chelate lipid molecule may be used to provide a unique functionality for attachment of other biomolecules to the surface of mica for AFM imaging.

Figure 9:
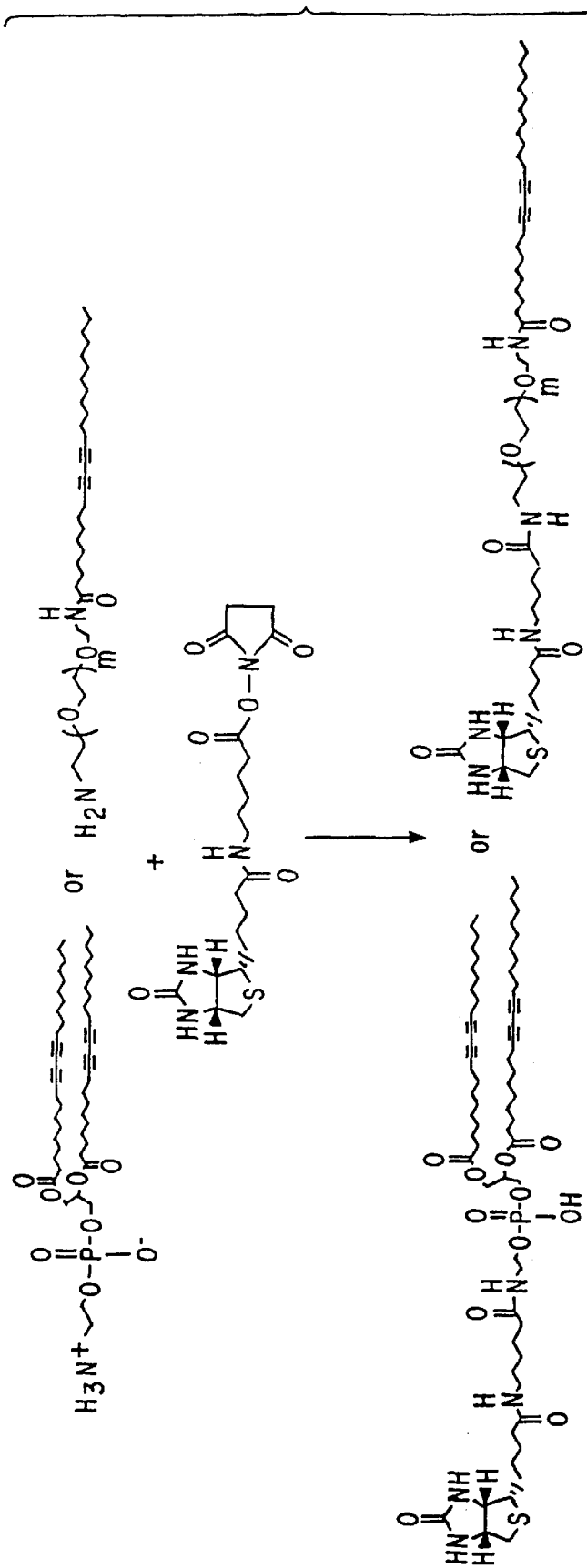
FIG. 9 shows the synthesis of biotinylated paramagnetic chelated lipids according to one embodiment of this invention.
Figure 10:
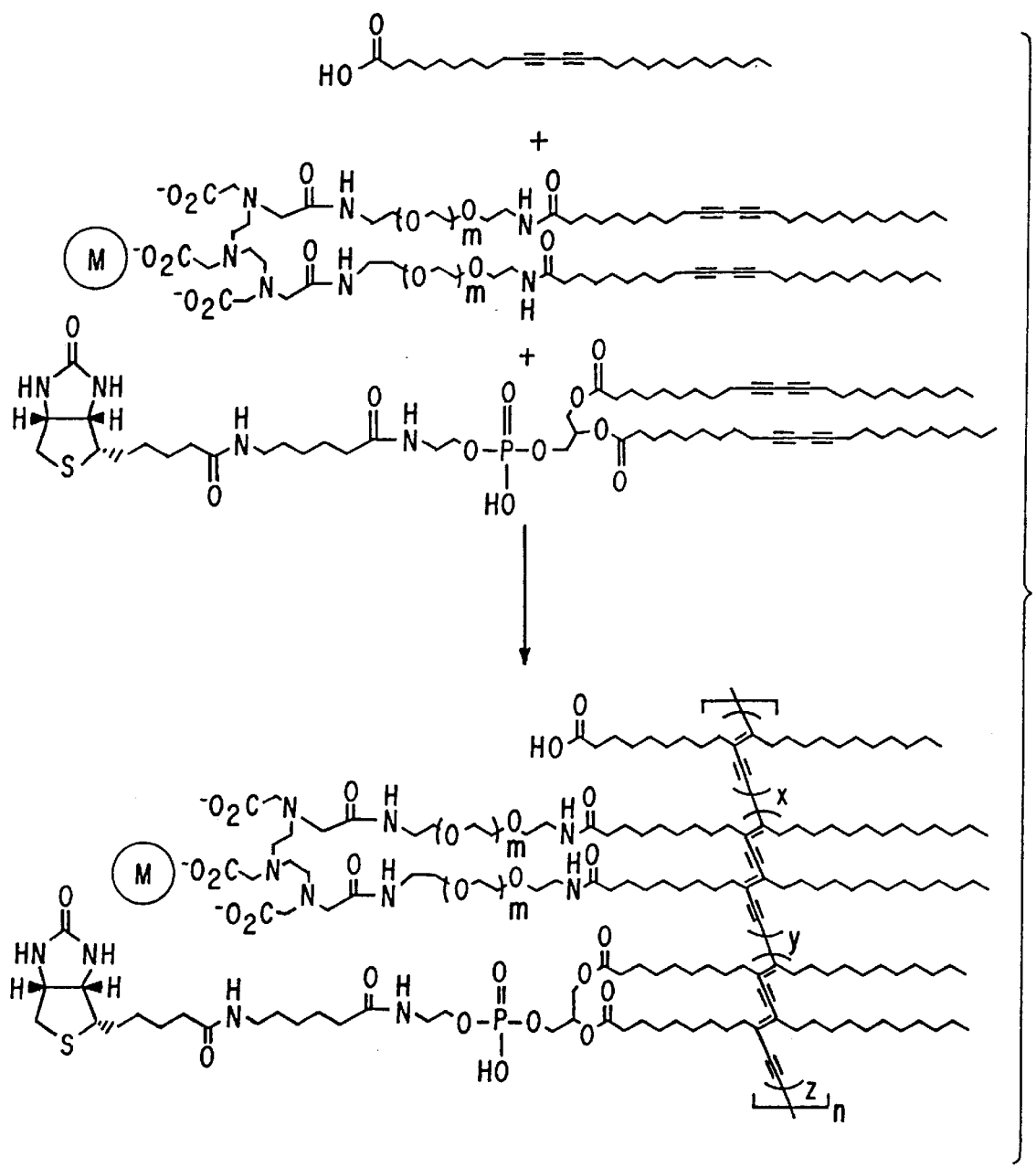
FIGS. 10 and 11 show formation of biotinylated paramagnetic polymerized liposomes using PDA and DAPC or DAPE.
Figure 11:
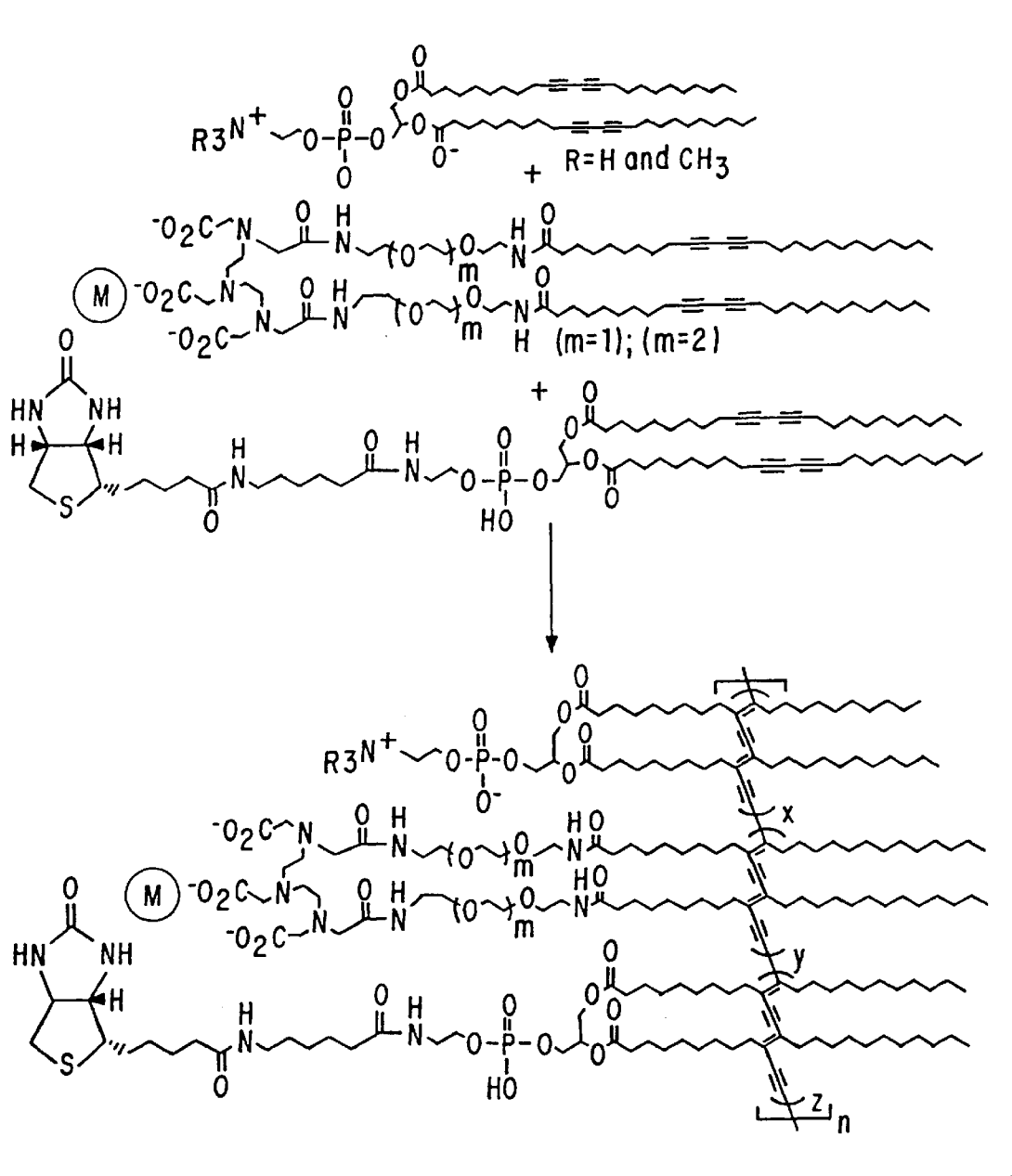

Targeted paramagnetic polymerized liposomes were produced from biotinylated or negatively charged liposomes to which biotinylated antibodies are attached through avidin, which has a high affinity for biotin and a high positive charge. In addition to biotin-avidin crosslinking, antibody-avidin conjugates can be attached to the polymerized liposome via charge-charge interactions similar to ion exchange. Commercially available diacetylene glycerophosphoethanolamine (DAPE) lipid is converted to its biotinylated analog by acylation of the amine terminated lipid with commercially available biotinylating agents, such as biotinamidocaproate N-hydroxysuccinimide ester or paranitrophenol esters, as shown in FIG. 9. The biotinylated paramagnetic polymerized liposomes are produced by incorporating the biotinylated lipid in an matrix of lipids of either PDA, DAPE or DAPC as shown in FIGS. 10 and 11, respectively. Negatively charge polymerized liposomes may be constructed by using pentacosadiynoic acid as a matrix lipid.

Figure 12:
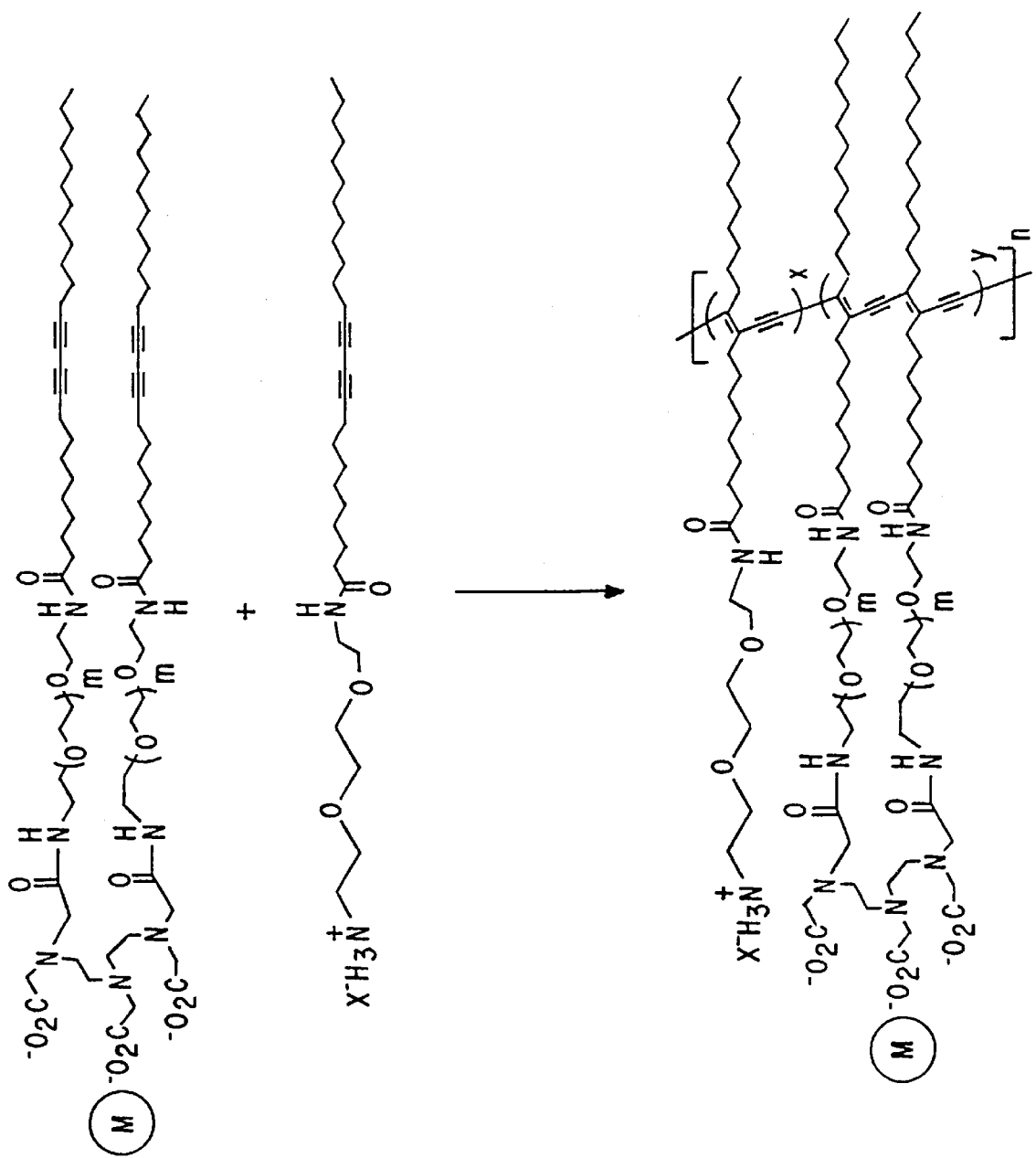
FIG. 12 shows formation of paramagnetic polymerized liposomes having positively charged functional groups.
Figure 13:
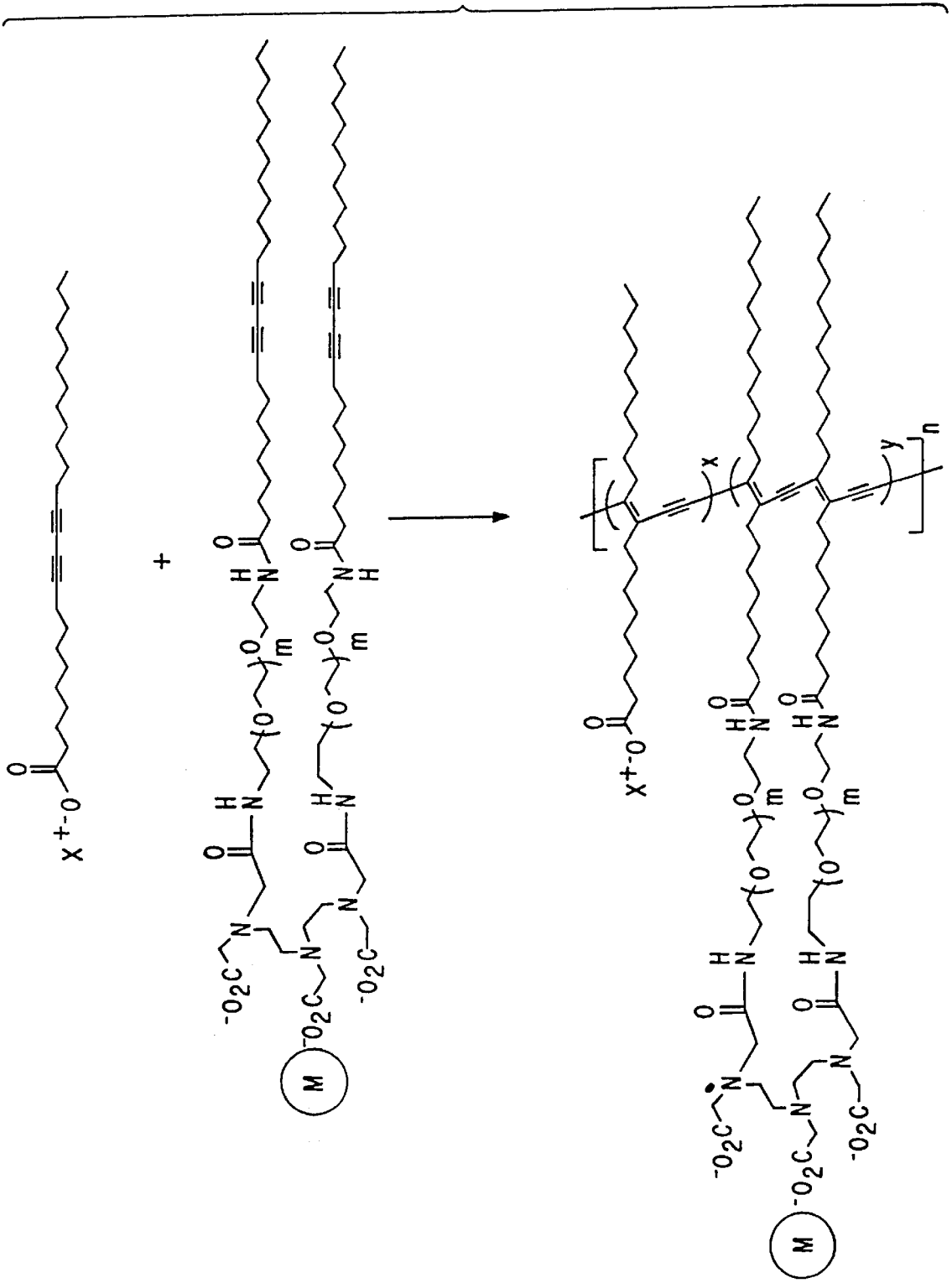
FIG. 13 shows formation of paramagnetic polymerized liposomes having negatively charged functional groups.
Figure 14:
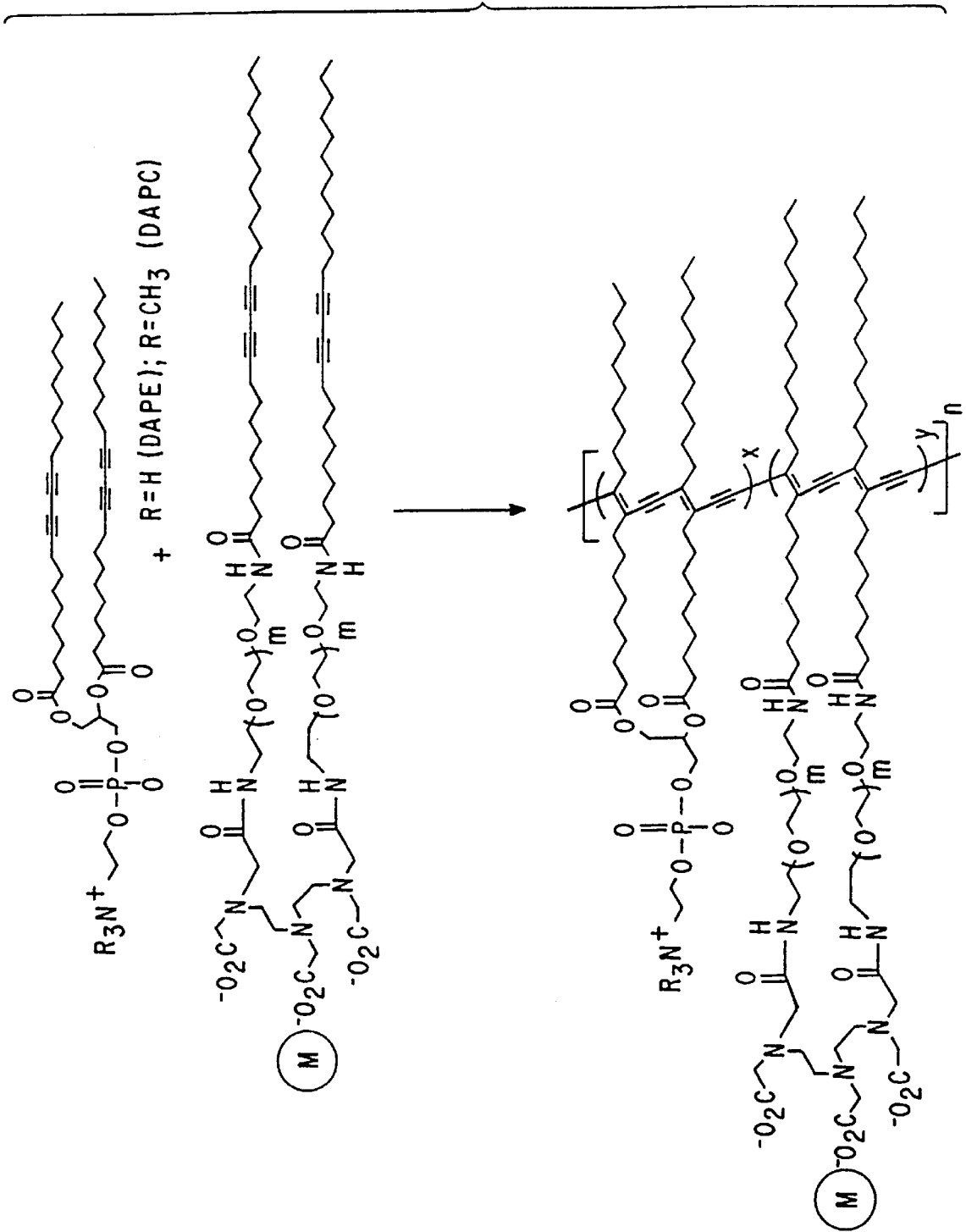
FIG. 14 shows formation of paramagnetic polymerized liposomes having zwitter ionic functional groups.

This invention includes a broad based group of agents having varied functionality which includes liposomes containing positively charged groups, such as amines as shown in FIG. 12, negatively charged groups, such as carboxylates as shown in FIG. 13, and neutral groups, such as zwitterions as shown in FIG. 14. These groups are important to control biodistribution blood pool half-life and non-specific adhesion of the particles.

Figure 15:
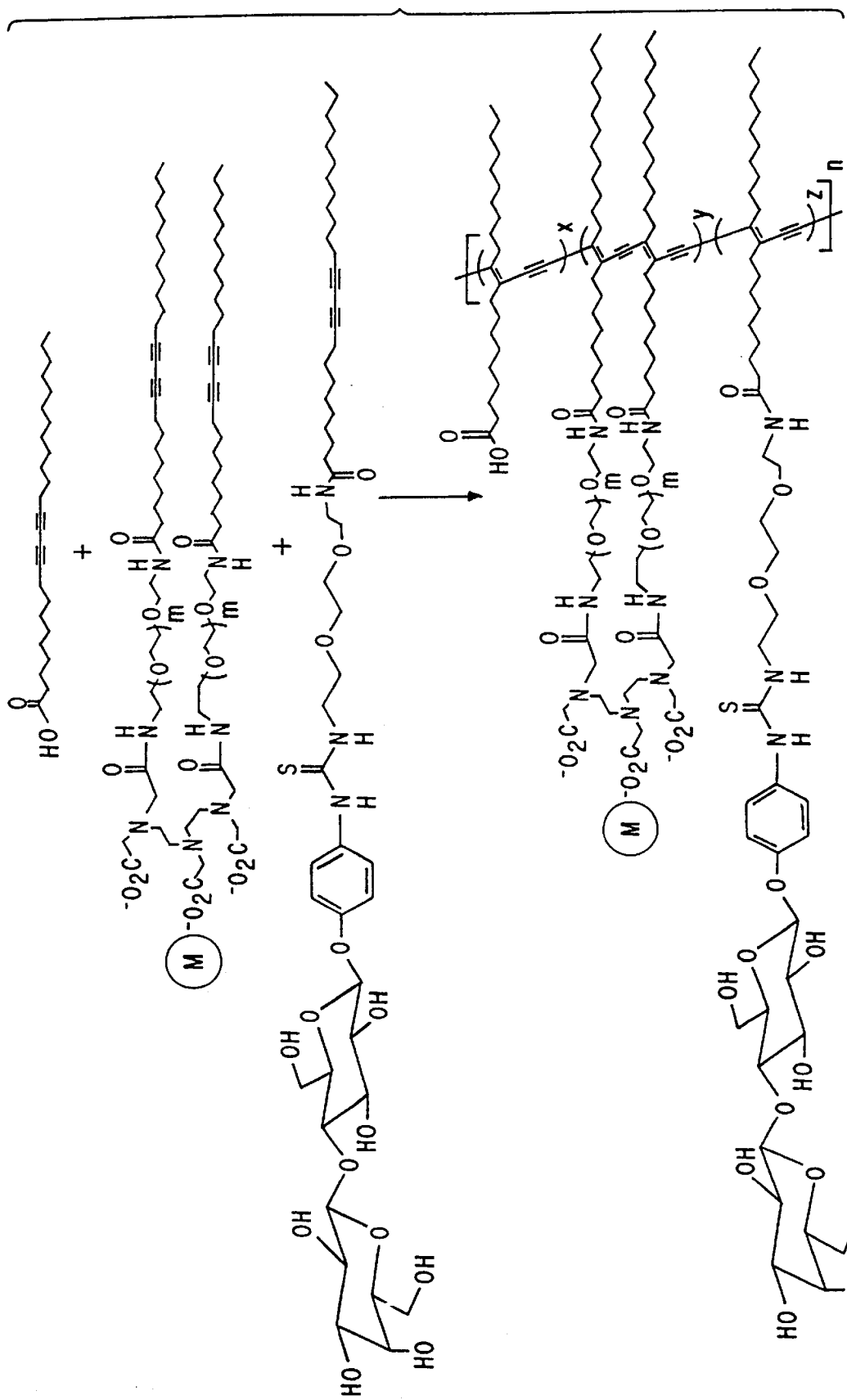
FIG. 15 shows formation of paramagnetic polymerized liposomes having lactose targeting groups.

Targeting groups of polymerized liposomes according to this invention may be ligands, such as carbohydrates, proteins, such as antibodies, peptides, antigenic determinants, or other receptor targeting groups. These head groups can be used to control the biodistribution, non-specific adhesion, and blood pool half life of the polymerized liposomes. For example, β-D-lactose has been attached on the surface, as shown in FIG. 15, to target the aloglysoprotein (ASG) found in liver cells which are in contact with the circulating blood pool. Targeting glycolipids are formed by converting the commercially available lipid (DAGPE) or the PEG-PDA amine shown in FIG. 4 into its isocyanate followed by treatment with triethylene glycol diamine spacer to produce the amine terminated thiocarbamate lipid which by treatment with the para-isothiocyanophenyl glycoside of the carbohydrate ligand produces the desired targeting glycolipids. This synthesis provides a water soluble flexible linker molecule spaced between the lipid that will form the internal structure or core of the liposome and the ligand that binds to cell surface receptors, allowing the ligand to be readily accessible to the protein receptors on the cell surfaces. The carbohydrate ligands can be derived from reducing sugars or glycosides, such as para-nitrophenyl glycosides, a wide range of which are commercially available or easily constructed using chemical or enzymatic methods. Paramagnetic polymerized liposomes coated with carbohydrate ligands can be produced by mixing appropriate amounts of individual lipids followed by sonication, extrusion and polymerization and filtration as described above and shown in FIG. 15. Suitable carbohydrate derivatized paramagnetic polymerized liposomes have about 1 to about 30 mole percent of the targeting glycolipid and filler lipid, such as PDA, DAPC or DAPC, with the balance being metal chelated lipid. Other lipids may be included in the polymerized liposomes to assure liposome formation and provide high contrast and recirculation.

Figure 16:
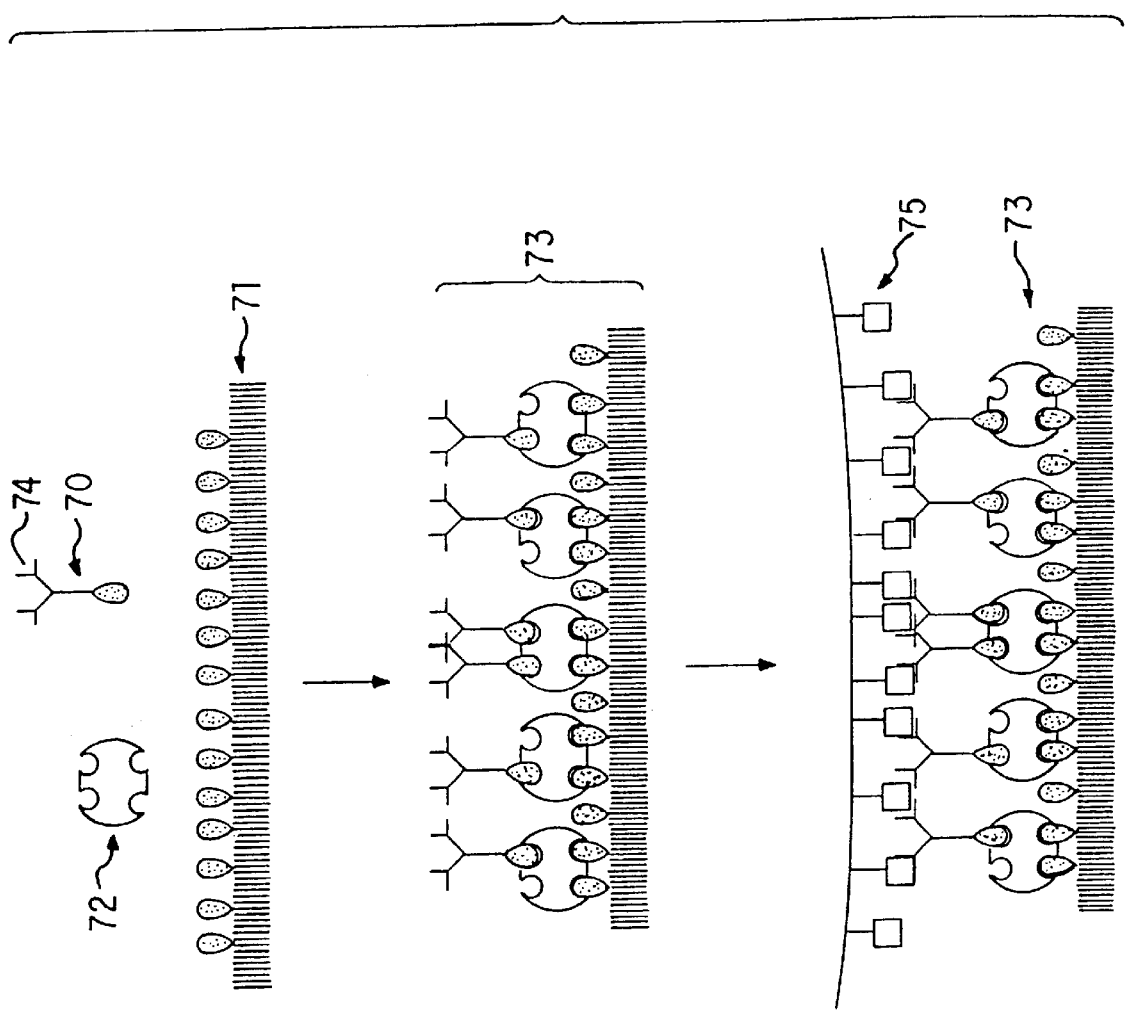
FIG. 16 schematically shows formation of paramagnetic polymerized liposomes having antibodies attached.

Antibodies may be attached to the particle by the biotin-avidin biotinylated antibody sandwich, as shown in FIG. 16, to allow a variety of commercially available biotintylated antibodies to be used on the polymerized liposome particles of this invention.

Biotinylated paramagnetic polymerized liposomes with a biotinylated anti-VCAM-1 antibody attached via a biotin avidin sandwich were produced in the manner described above. This targeted paramagnetic polymerized liposome binds to VCAM-1, a leukocyte adhesion receptor on the endothelial surface which is upregulated during inflammation. In vitro histology demonstrated specific interactions between the polymerized liposomes and the inflamed brainstem tissue from a mouse with allergic autoimmune encephalitis. The formation of such biotinylated antibody coated polymerized liposomes and their attachment to in vivo cell receptors is schematically shown in FIG. 16. As shown in FIG. 16, the biotinylated antibody 70 having functional group 74 is attached to the biotinylated lipid surface 71 through bridge 72 of avidin or streptavidin to form antibody coated polymerized liposomes 73. The functional group 74 of antibody 70 is attached in vivo to an endothelium receptor 75, thereby attaching the paramagnetic polymerized liposome to the endothelium for external detection.

Figure 17:
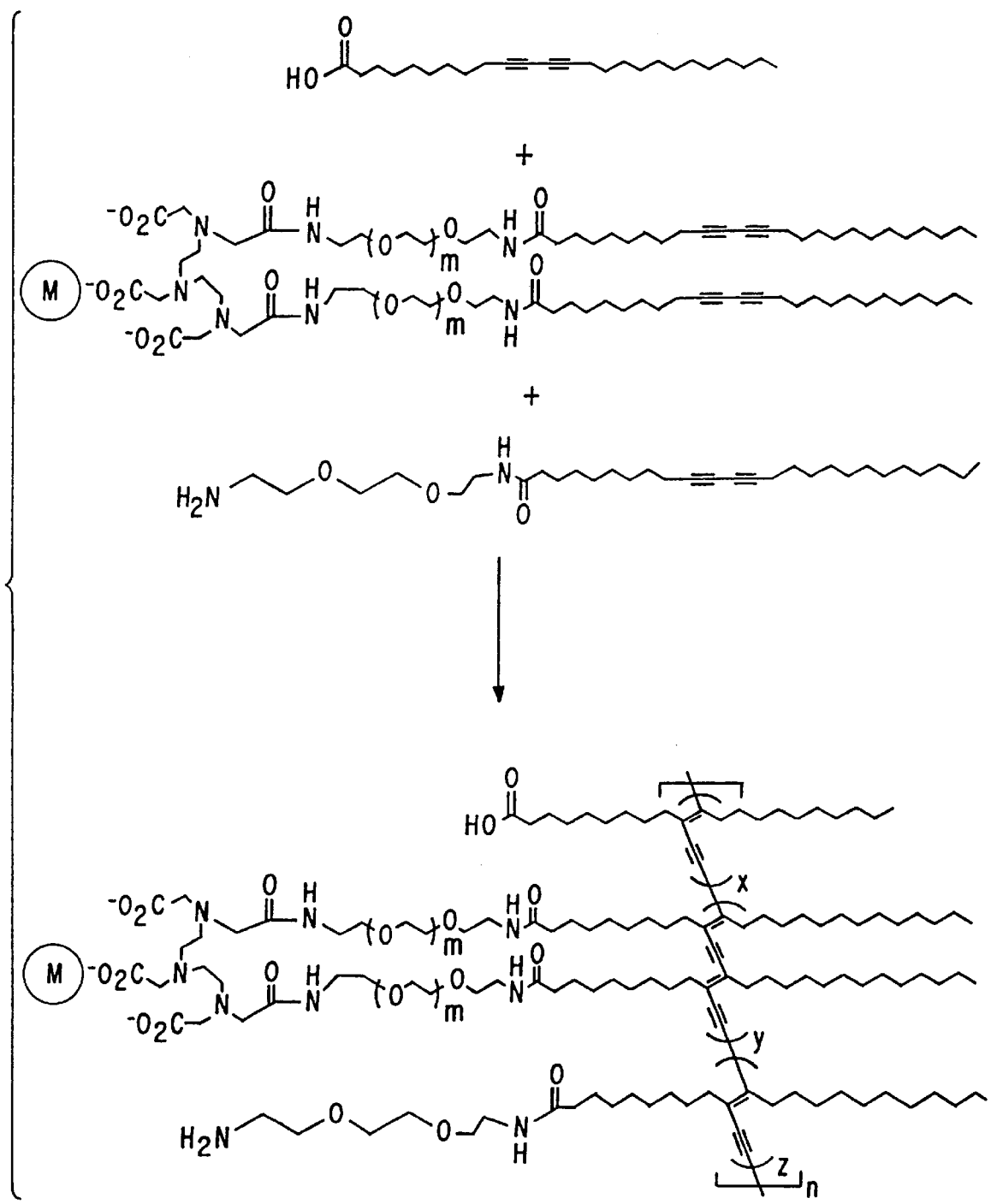
FIGS. 17 and 18 show formation of liposomes that can be used for direct attachment of oxidized antibodies by an amine via reductive amination and hydrazone formation via alkyl hydrazine.
Figure 18:
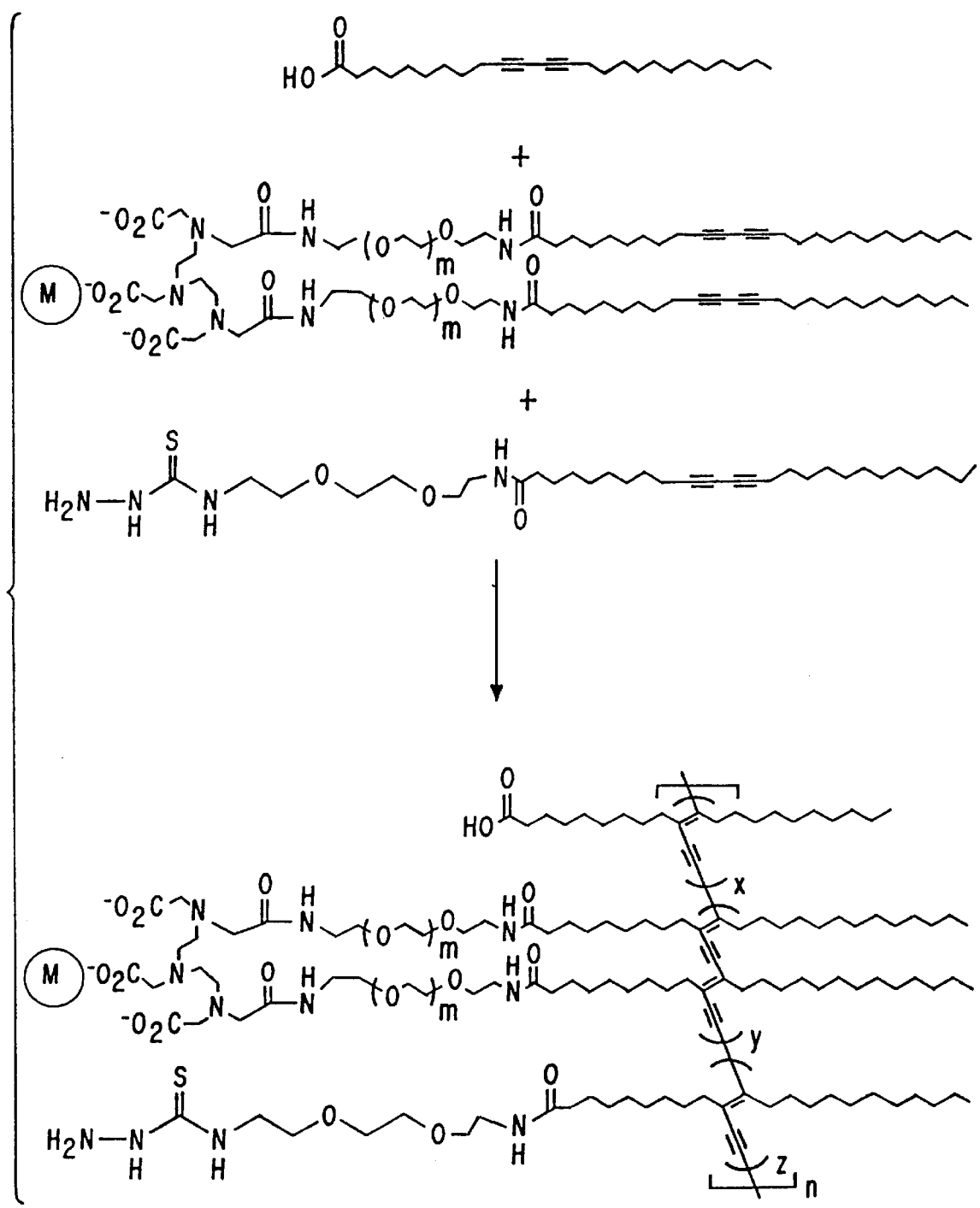

Antibodies may also be attached by "direct" methods. In particular, wherein the liposome contains a group, such as an amine or hydrazine derivatives, that reacts with aldehydes on oxidized antibodies and olgosaccharides. We have constructed liposomes containing amine, FIG. 17, and hydrazine, FIG. 18, head groups for this purpose. Antibodies can also be attached by charge-charge interaction such as ion exchange. In this case, the antibody is bound to a positively charged protein, such as, for example, avidin and this complex ion exchanged onto negatively charged polymerized liposomes.

Although the embodiments of this invention using image intensifiers have been described and specifically exemplified primarily with respect to polymerized liposomes having an attached metal for magnetic resonance imaging, it should be clear to one skilled in the art that other detection materials may be attached in a similar manner, such as a radioisotope for radioisotope imaging, a heavy metal for x-ray imaging, or a chromophore for optical imaging and are meant to be included in this invention. We have attached Indium to paramagnetic polymerized liposomes, as described in Storrs, Richard W., et al, JMRI, (1995) incorporated herein by reference, supra. Likewise, in other embodiments, any suitable functional group may be attached to liposomes incorporated into the polymerized liposomes of this invention to provide attachment to specified targets, in vitro and in vivo, to obtain concentration of the image contrast agent at the specified target site.

We have found that use of antibody-conjugated polymerized liposomes, according to this invention, provides an in vitro ultra-sensitive diagnostic assay of the presence of specific antigens in solution. Monoclonal antibodies are conjugated to the surface of polymerized liposomes by combination of avidin with biotinylated antibody followed by addition of polymerized liposomes to form antibody-conjugated polymerized liposomes. The size distribution of these particles is then determined by photon correlation spectroscopy (PCS), using for example, a Coulter N4+ submicron particle analyzer. The sample containing an antigen of interest is added to the antibody-conjugated polymerized liposomes and allowed to incubate in solution. The multivalent antibody-conjugated polymerized liposomes recognize the antigen and microscopic agglutination occurs and is detected by a change in size distribution as detected by photon correlation spectroscopy.

Polymerized liposomes of this invention having a chelator head group chelated to spectroscopically distinct ions, such as Europium, provide high sensitivity methods for ELISA based in vitro assays which do not require radiochemistry. Europium labelled polymerized liposomes of this invention, in an ELISA based system, can be detected at concentrations of $10^{-21}$ molar using time-resolved flourscence spectroscopy.

The expression of glycoproteins on cell surfaces may be detected according to this invention by use of polymerized liposomes having a head group bearing a fluorophore. Polymerized liposomes may be constructed according to this invention having a negative charge so that they adhere to cell surfaces expressing positively charged proteins. Pentacosadiynoic acid or other carboxylic acid terminated lipids can be used for this purpose. In similar manner, polymerized liposomes may be constructed having a positive charge. In another embodiment, a lipid containing a fluorophore head group, such as Texas Red, was constructed and incorporated into polymerized liposomes. Fluorophore head group polymerized liposomes may be constructed by incorporating an amine containing lipid, such as pentacosadiynoic acid-$(PEG)_4$—$NH_2$, into the liposome and having a commercially available fluorophore attached to the liposome via the amine.

Antibody-conjugated paramagnetic polymerized liposomes of this invention achieve in vitro and in vivo targeting of specific molecules associated with specific body tissues and specific molecules associated with specific bodily functions and pathologies to provide sufficient signal enhancement for detection by magnetic resonance imaging. Such in vivo imaging of various disease or developmentally associated molecules permits following the relationship of these molecules to disease progression, their time course of progression, and their response to pharmacologic interventions. Characterization of these responses in individual animals simplifies assessment of the interventions, since expression and regression of the target can be confirmed as it relates to disease outcomes. As a diagnostic tool, this technique detects disease at early stages, thereby enabling more effective treatment. The paramagnetic polymerized liposomes of this invention are suitable for combination of imaging and delivery of drugs for therapeutic treatments. Various agents can be encapsulated or attached to the surface of polymerized liposomes for delivery to specific sites in vivo. By using target-specific drug/paramagnetic polymerized liposomes of this invention, the drug delivery can be simultaneously visualized by magnetic resonance imaging.

The targeted paramagnetic polymerized liposomes of this invention provide non-invasive in vivo investigation by providing magnetic resonance imaging of tissues to visualize endothelial antigens which characterize disease at the molecular level in nearly real time. Endothelial cell adhesion molecules serve as a suitable target for magnetic resonance imaging, since the early and specific upregulation of vascular cell adhesion molecules occurs in a variety of diseases. Targeted paramagnetic polymerized liposomes which recirculate in the vasculature may include endothelial antigens which interact with the cell adhesion molecules to retain a number of the the targeted paramagnetic polymerized liposomes at the desired location. The high concentration of magnetic resonance image enhancement agents in the polymerized liposomes of this invention render possible in vivo non-invasive magnetic resonance imaging of pathologic changes. To our knowledge, no magnetic resonance image contrast enhancement agent specific for changes in endothelial receptor expression have been described. The polymerized liposomes of this invention are particularly well suited since they maintain their integrity in vivo, recirculate in the blood pool, are rigid and do not easily fuse with cell membranes, and serve as a scaffold for attachment of both the antibodies and the paramagnetic contrast ion for magnetic resonance imaging. The size distribution, particle rigidity and surface characteristics of the polymerized liposomes can be tailored to avoid rapid clearance by the reticuloendothelial system and the surface can be modified with ethylene glycol to further increase intravascular recirculation times. We have found that the paramagnetic polymerized liposomes have blood pool half-lives of about 20 hours in rats.

In one embodiment, the site-specific paramagnetic polymerized liposome having attached monoclonal antibodies for specific receptor targeting may be used to visualize intercellular adhesion molecule-1, ICAM-1, upregulation in murine experimental autoimmune encephalitis, an animal model for multiple sclerosis. Such an agent can also enable imaging of endothelial antigen expression and regulation in vivo, permitting early detection and treatment of diseases like multiple sclerosis in humans.

The following specific examples are set forth in detail to illustrate the invention and should not be considered to limit the invention in any way.

EXAMPLE I

Paramagnetic polymerizable lipids having $Gd^{+3}$ and PDA headgroups were synthesized by first preparing the succinimidyl ester by stirring pentacosadiynoic acid (PDA, Lancaster; 10.0 g, 26.7 mmol), N-hydroxysuccinimide (NHS, Aldrich; 5.00 g, 43.4 mmol) and 1-(3-dimethylaminopropyl)-3-ethylcarbodiimide hydrochloride (EDC, Aldrich; 6.01 g, 31.3 mmol) in 660 ml $CH_2Cl_2$ at room temperature and shielded from light. The reaction was followed by thin layer chromatography ($CHCl_3$/MeOH, 8/1) and deemed complete after approximately 5 hours. The solution was washed with water, 1% HCl, saturated sodium bicarbonate and brine. The organic phase was then dried with $MgSO_4$, filtered, and concentrated under reduced pressure to yield the N-succinimidyl 10,12-pentacosadiynoic acid ester as a slightly yellow solid (10.84 g; 23.0 mmol; 86%).

The succinimidyl ester was dissolved in $CH_2Cl$ (250 ml) and then slowly added, in dropwise fashion, to a stirred solution of 1,11-diamino-3,6,9-trioxyundecane (9.13 g, 61.6 mmol; Texaco) in $CH_2Cl_2$ (110 ml) over a 16 hour period at room temperature and shielded from light. The resulting solution was concentrated to a thick slurry and chromatographed on silica gel using a gradient of $CHCl_3$/MeOH (1/0 to 8/1). The homogeneous fractions were pooled and evaporated under reduced pressure to result in the desired lipid, (1'-N-,11'-amino-3', 6'-dioxyundecanoyl)-10,12-pentcosadiynamide, as a white solid (4.40 g; 38.1%). This product must be handled with care as it spontaneously polymerizes in the solid state when it is pure. It is more stable in solution at 4° C., but should be used as soon as possible after preparation.

The above-prepared aminoamide (4.40 g; 8.78 mmol) and DTPAA (1.56 g; 4.37 mmol) were stirred in pyridine (25 ml) overnight, shielded from the light. The solvent was evaporated and the residue coevaporated with methanol to dryness twice to result in an oil free from pyridine. The residue was dissolved in acetone and the product allowed to precipitate from solution after overnight storage at 4° C. Filtration resulted in the desired chelator lipid, bis-N-[2-ethyl-N-'carboxymethyl,N'-carboxymethyl(1'-N-''',11'-N''''-3',6'-dioxyundecanoyl)amide-1'',12''-pentacosadiynamide]-glycine, as a white amorphous powder (3.30 g; 55%). Further purification can be achieved by crystallization from methanol (40 mg/ml; m.p. 128.5–129.5° C. (decomp.)).

The chelator lipid, as prepared above, was heated with $GdCl_3 \cdot 6H_2O$ or $DyCl_3 \cdot 6H_2O$ (0.95–0.98 equiv.) in methanol. The solvent was evaporated and the residue coevaporated with methanol to remove all traces of generated HCl. The resulting lanthanide chelate lipids, bis-N-[2-ethyl-N-'carboxymethyl,N'-carboxymethyl(1'-N-''',11'-N''''-3', 6'-dioxyundecanoyl)amide-1'',12''-pentacosadiynamide]-glycine-lanthanide,gadolinium or dysprosium, complexes, were then stored as methanolic solutions at 4° C., shielded from light. The identity of the synthesized chelates was confirmed by FAB-MS.

Paramagnetic polymerized lipids were formed by mixing a 1:9 molar ratio of the above prepared paramagnetic polymerizible lipids with di-tricosadiynoyl phosphatidyl choline (Avanti Polar Lipids, Birmingham, Ala.) in an organic solvent methyl alcohol and chloroform (⅓) and evaporating the solvent and rehydrating with distilled water to 30 mM diacetylene (15 mM total lipid). Following sonication with a 450 W probe-tip sonicator (Virsonic 475, Virtis Corp., Gardiner, N.Y.) set at a power setting of 2½ units for 30 to 60 minutes without temperature control, the suspension of lipid aggregates was extruded ten times through two polycarbonate filters with pores of 0.1 μm diameter (Poretics, Livermore, Calif.) at 56° C. using a thermobarrel extruder (Lipex Biomembranes, Vancouver, BC). This solution was spread thinly on a petri dish in a wet ice slush and irradiated with a UV lamp, 2200 μWatt/cm² held 1 cm over the solution while stirring. The solution turned orange using DAPC over the course of a one hour irradiation, due to the absorption of visible light by the conjugated ene-yne system of the polymer. The paramagnetic polymerized liposomes passed easily through a 0.2 μm sterilizing filter and were stored in solution until use. The paramagnetic polymerized lipid suspensions prepared in this manner have been found to be stable for many weeks at 4° C.

Figure 7:
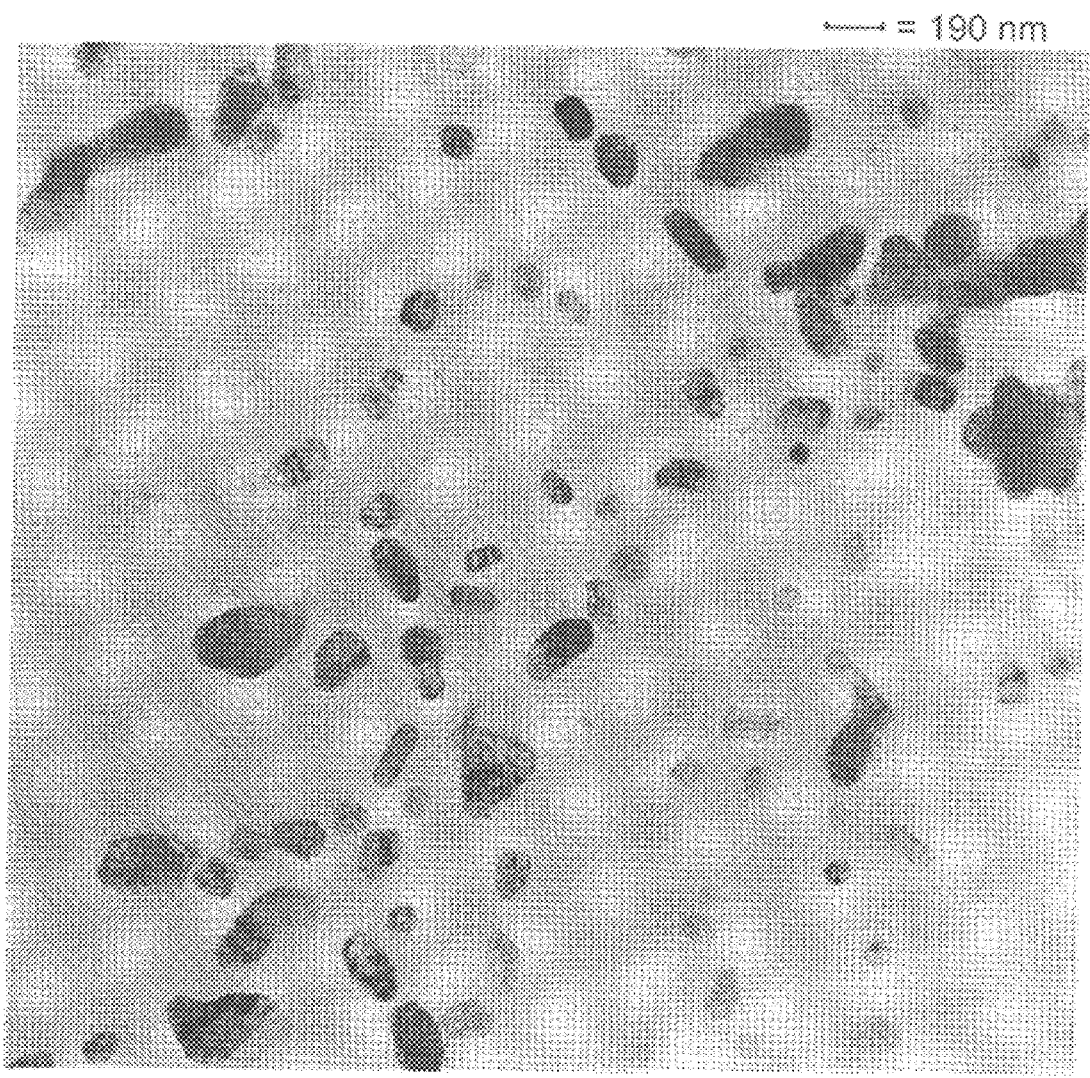
FIG. 7 is a transmission electron micrograph of polymerized liposome particles.
Figure 8:
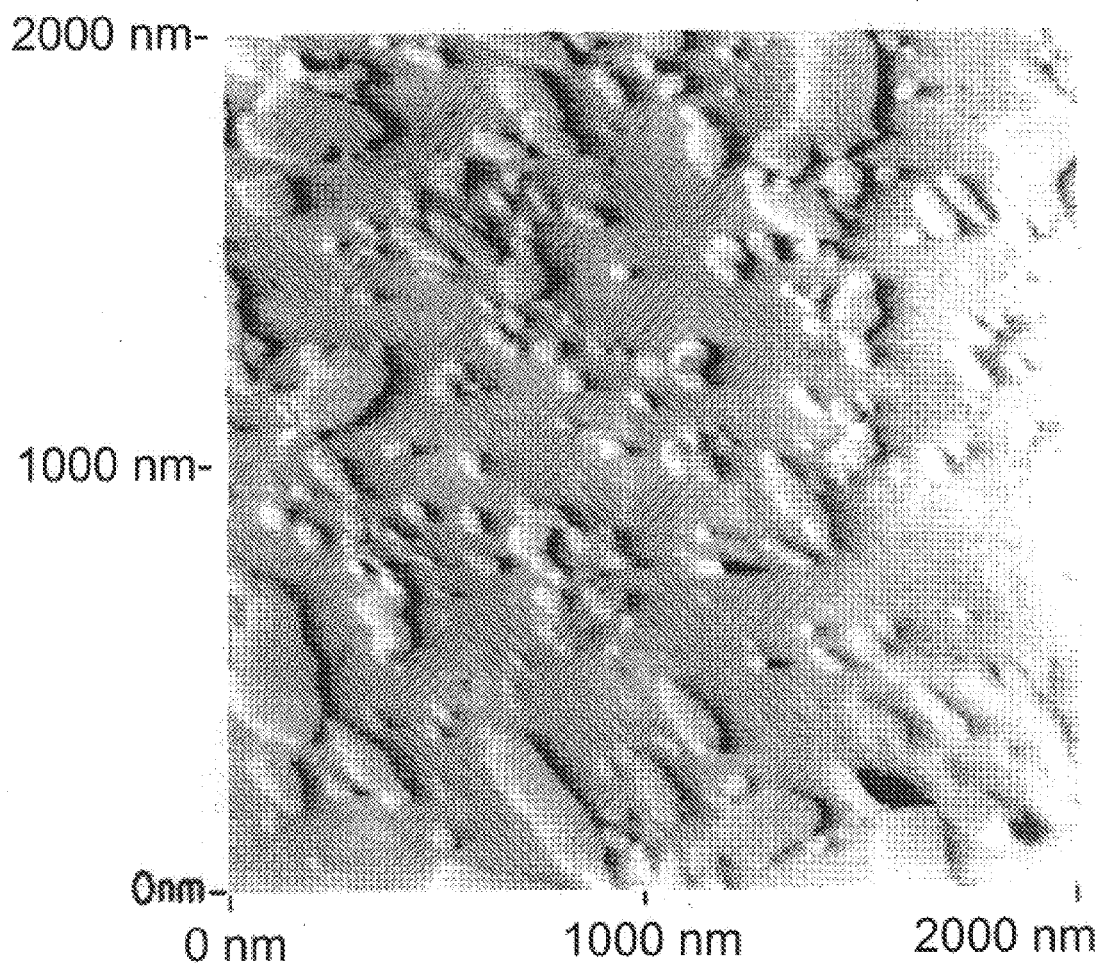
FIG. 8 is an atomic force micrograph in color of polymerized liposome particles.

The size and shape of the paramagnetic polymerized liposomes have been ascertained by transmission electron microscopy and by atomic force microscopy, as shown in FIGS. 7 and 8. They appear as prolate ellipsoids with minor axes on the order of the membrane pore and major axes about 50 percent greater.

EXAMPLE II

The procedures of Example I were followed except that instead of using DAPC, pentacosydiynoic acid (PDA) was used as the filler lipid. The solution turned blue over the course of one hour irradiation. The resulting polymerized liposomes had the same general properties as reported in Example I.

EXAMPLE III

Two month old Lewis rats were anaesthetized either with 40–75 mg/Kg dose of sodium pentobarbitol i.p. or by 1.5% isoflurane by inhalation. Paramagnetic polymerized liposome, as prepared in Example I, was administered i.v. over 60–90 seconds through a 24 G catheter in a laterial tail vein at a dose of 0.015 mmol $Gd^{+3}$/kg body weight.

Axial magnetic resonance images of the abdomen were obtained prior to paramagnetic polymerized liposome administration and periodically for up to 2 hours post administration. All magnetic resonance images were obtained using an OMEGA-CSI imager (GE, Milwaukee, Wis.) at field strengths of 2.0 or 4.7 Telsa using the standard spin-echo acquisition sequence. T1 weighted images were obtained using a repetition time (TR) of 400 ms, echo time (TE) of 18 ms, and 2 excitations (NEX) per 128 phase encoding steps, completing a 256×128 data matrix in under 2 minutes. Slice thickness (ST) was 2 mm and the interslice gap was 2 mm. Four axial slices were acquired in multislice mode, with the slice position chosen so that the liver appeared in the first two slices and the kidneys appeared in the fourth, most inferior slice. These images were often supplemented by a second set of images interleaving the first set. Two phantoms, test tubes containing 10 mM $Ni(NO_3)$ or 1 mM $GdCl_3$, were placed longitudinally beneath the rats and were imaged concurrently to monitor instrumental variations. The image intensity of the phantoms varied less than 5% in all of the experiments.

Data analysis was performed using the program XCINEMA (Lucas MRS Center, Stanford University, Stanford, Calif.) Region of interests (ROI) were drawn conservatively within each organ, and the intensity of the same region at each time point was measured. The intensity data post contrast was normalized to the intensity of the ROI prior to contrast administration and the normalized data for each time point averaged across six experiments on four rats each.

The injected paramagnetic polymerized liposomes were well tolerated by the rats with no significant adverse effects observed. The rats continued to gain weight in the days succeeding administration and exhibited normal behavior and activity. Hematuria was observed only in the first urination following recovery from the anesthesia, likely as a result of osmotic shock since the injection preparation contained no added salts. Repeated administration of the paramagnetic polymerized liposome preparation to the same rat did not affect tolerance or contrast enhancement.

Figure 19:
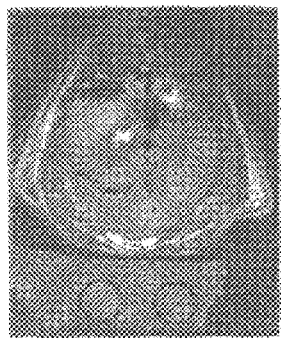
FIGS. 19–21 are magnetic resonance images of rat livers as described in Example III.
Figure 20:
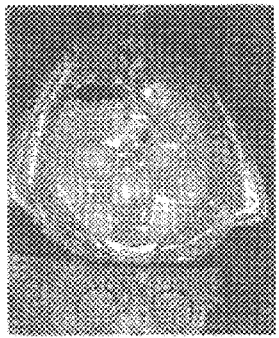
Figure 21:
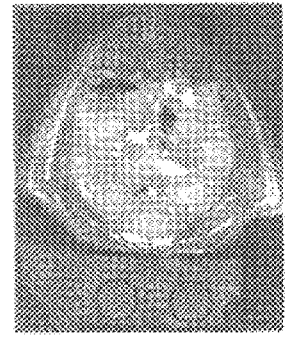
Figure 22:
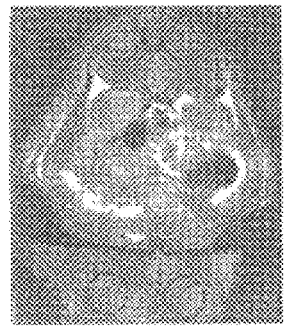
FIGS. 22–24 are magnetic resonance images of rat kidneys as described in Example III.
Figure 23:
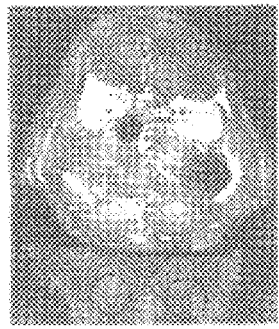
Figure 24:
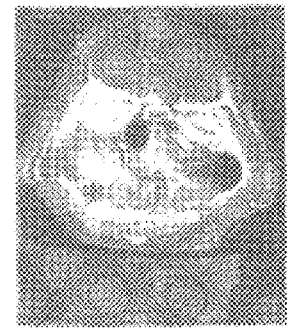

Representative magnetic resonance images of the rat liver and kidneys are shown in FIGS. 19–21 and 22–24, respectively: prior to administration shown in FIGS. 19 and 22; 5 minutes after administration shown in FIGS. 20 and 23; and 60 minutes after admistration shown in FIGS. 21 and 24. The increase in T1-weighted signal intensity is readily apparent in both the liver and kidneys and has been found to persist throughout a 90 minute period.

Figure 25:
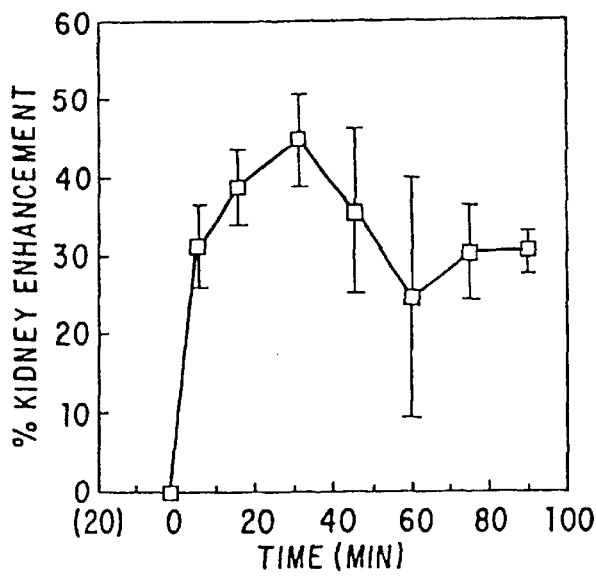
FIG. 25 is a graph showing average enhancement of magnetic resonance image intensity in rat kidneys versus time.
Figure 26:
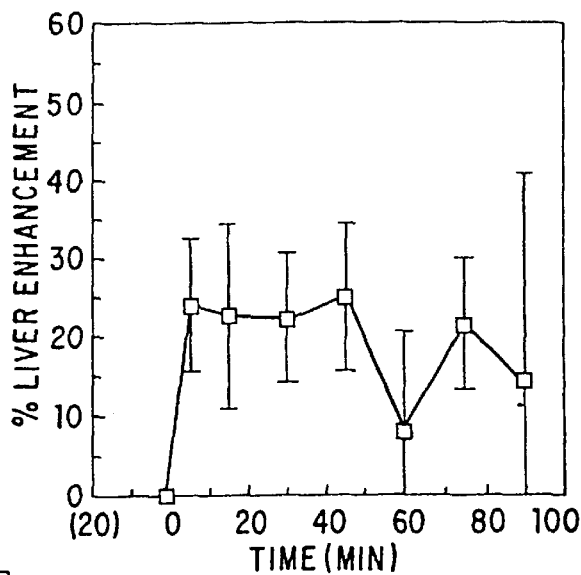
FIG. 26 is a graph showing average enhancement of magnetic resonance image intensity in rat livers versus time.
Figure 27:
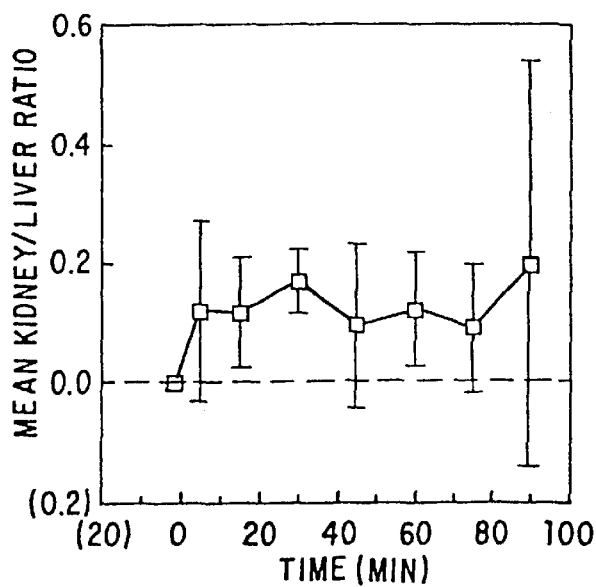
FIG. 27 is a graph showing the ratio of enhancement shown in FIGS. 25–26 of kidneys to liver, relative to precontrast enhancement versus time.

The average enhancement of magnetic resonance intensity for ROIs within the kidney and liver for all six experiments are shown in FIGS. 25 and 26, respectively. These data were not corrected for the intensity variation of the phantoms. The kidneys enhanced an average of 34% over 90 minutes, reaching a maximum of 45% enhancement at about 30 minutes. The liver enhanced an average of about 20% over 90 minutes, reaching a maximum of about 23% at about 5 to 40 minutes. FIG. 27 shows the ratio of enhancement, relative to precontrast enhancement, of the kidneys to liver, showing the time course of enhancement of these two organs to be similar, indicating that the enhancement agent was not selectively eliminated by either of these organs during the 90 minute experimental time period. This indicates recirculation of the enhancement agent in the blood pool of the rats.

This Example illustrates that the enhancement seen in the liver and kidneys, both highly vascularized organs, is easily visible even at a dose of 0.015 mmol $Gd^{+3}$/kg, one tenth the normal clinical dose of Gd-diethylenetriamine pentaacetic acid for magnetic resonance imaging. The high magnetic resonance sensitivity of the paramagnetic polymerized lipid preparation results from: (1) The particulate nature of the polymerized lipid slows the correlation time for reorientation of the $Gd^{+3}$ ion, which concentrates the power of the relaxation-effecting magnetic fluctuations in the regime of the water proton Larmor frequency and results in a higher molar relaxivity per $Gd^{+3}$ ion of 11.2 $mM^{-1}s^{-1}$, as compared with Gd-diethylenetriamine pentaacetic acid of 4.2 $mM^{-1}s^{-1}$; and (2) The paramagnetic polymerizied lipid particles are confined to the blood pool and do not leak into the interstitial spaces, as does Gd-diethylenetriamanine pentaacetic acid. The reduced volume of distribution leads to a relatively increased blood pool concentration of gadolinium for the paramagnetic polymerized liposomes, as compared to a similar body weight dosage of Gd-diethylenetriamine pentaacetic acid.

Extended recirculation of the paramagnetic polymerized liposomes and their lack or absence of retention by the kidneys and liver is evident from the prolonged magnetic resonance intensity enhancement and the constant ratio of enhancement for these organs, as compared to Gd-diethylenetriamine pentaacetic acid, which is eliminated from the blood pool within a few minutes. The prolonged recirculation of the paramagnetic polymerized liposomes results from reduction in phagocytosis by macrophages of the reticuloendothelial system by selection and control of the particle size, particle rigidity and, perhaps, by use of polyethylene linkers for attachment of the $Gd^{+3}$ ion. Evasion of the reticuloendothelial system is probably complemented by evasion of the immune system by use of surface groups, such as, for example, choline, which is the major component of mammalian cells, as the matrix for presentation of the paramagnetic and ligand-bearing paramagnetic polymerized liposomes of this invention.

EXAMPLE IV

Antibodies towards the specific immunoglobin, anti-goat γ-IgG, were conjugated to polymerized liposomes to form antibody-conjugated polymerized liposomes for use in in vitro diagnostic applications.

Lipid components of: 60% pentacosadiynoic acid filler lipid, 29.5% chelator lipid, 10% amine terminated lipid and 0.5% biotinylated lipid were combined in the indicated amounts and the solvents evaporated. Water was added to yield a solution that was 30 mM in acyl chains. The lipid/water mixture was then sonicated for at least one hour. During sonication, the pH of the solution was maintained between 7 and 8 with NaOH and the temperature was maintained above the gel-liquid crystal phase transition point by the heat generated by sonication. The liposomes were transferred to a petri dish resting on a bed of wet ice and irradiated at 254 nm for at least one hour to polymerize. The polymerized liposomes were collected after passage through a 0.2 μ filter. To form the antibody conjugated polymerized liposomes, 2.3 μg avidin was combined with 14.9 μg biotinylated antibody in phosphate buffered saline in about 1:3 molar ratio and incubated at room temperature for 15 minutes. This solution was combined with 150 μL of the above formed polymerized liposomes and incubated at 4° C. overnight to form the antibody-conjugated polymerized liposomes. The total number of antibody-conjugated polymerized liposomes in a 40 μl aliquot was found to be about $1.4 \times 10^{11}$ as determined by light scattering and theoretical calculations based on the size of the particles and protein and amount of lipid used in the preparation. The antibody-conjugated polymerized liposomes were analyzed by photon correlation spectroscopy using a Coulter N4+ submicron particle analyzer and shown to have a mean diameter of 262 nm. Then 9.6 μg of agglutinating antibody, goat IgG, was added to a 40 μl aliquot of anti-goat γ-IgG-conjugated polymerized liposomes, as prepared above, and incubated for about 1 hour. After this incubation, 53% of the antibody-conjugated polymerized liposomes had agglutinated as demonstrated by the appearance of a new group of particles with a mean diameter of 1145 nm, as determined by photon correlation spectroscopy. The antibody-conjugated polymerized liposomes thereby provide a simple and very sensitive in vitro assay for the presence of specific antigens in solution.

EXAMPLE V

Lipids containing a DTPA chelator head group were constructed as described in Storrs, et al, JACS, (1995) incorporated herein supra, paragraph spanning pages 7305–7506, for compound 4 and 1b and chelated to $Eu^{+3}$ ions and formed into polymerized liposomes at a level of 1%. A wide variety of suitable chelating agents for spectroscopically distinct ions are known to the art as, for example, as described in U.S. Pat. Nos. 4,259,313; 4,859,777; 4,801,504; 4,784,912; and 4,801,722. The Europium labelled polymerized liposomes were serially diluted with buffer and detected using time-resolved flourescence spectroscopy, detecting $Eu^{+3}$ labeled polymerized liposomes down to concentrations of 10–21 molar in an ELISA based system.

EXAMPLE VI

Polymerized liposomes based upon pentacosadiynoic acid were constructed having a negative charge. No exogenous fluorescent probes were used and only the intrinsic fluorescence of the polymerized liposomes, emission at 530–680 nm, was relied upon for detection. The polymerized liposomes were incubated with endothelial cells expressing P-Selectin, a protein that binds charged entities, and then analyzed using flow cytometry. Flow cytometry detected the polymerized liposomes adhered to the endothelial cells.

EXAMPLE VII

A lipid containing a fluorophore head group, such as, for example, Texas Red, was constructed. Suitable lipids are, for example, $PDA(PEG)_3-NH_2$/carboxylic acids and hydraziene derivatives and suitable fluorophore head groups are, for example, Texas Red and FITC. This material was incorporated into polymerized liposomes at a level of 0.5%. 200 µg Texas Red sulfonyl chloride in acetonitrile was added to 600 µl polymerized liposomes, 30 mM in acyl chain, on 0.01M sodium bicarbonate buffer, pH9, and reacted at room temperature for 2 hours. The labeled polymerized liposomes were then purified by gel filtration (Sephadex G-25, Sigma, St. Louis, Mo.) using PBS as eluent. An anti-ICAM-1 antibody was then attached to the Texas Red labelled polymerized liposomes in the same manner as described in Example IV and then incubated with activated endothelial cells expressing ICAM-1 and analyzed using fluorescent microscopy. Using this approach, $10^5$ to $10^6$ Texas Red molecules can be linked to each antibody resulting in dramatic increase in sensitivity of the assay. The antibody conjugated polymerized liposomes can be easily seen bound to the activated endothelium, thus simplifying the methodology for assaying cell surface glycoproteins.

EXAMPLE VIII

To conjugate monoclonal antibodies to paramagnetic polymerized liposomes, we constructed paramagnetic polymerized liposomes containing biotinylated lipids. Avidin, a biotin binding protein, was then used to bridge biotinylated antibodies to biotin on the particle surface. Alternatively, anionic polymerized liposome particles may be constructed and antibodies conjugated to cationic proteins, such as avidin, are then exchanged onto the particles.

Lipid components of: 60% pentacosadiynoic acid filler lipid, 29.5% $Gd^{+3}$ chelator lipid, 10% amine terminated lipid and 0.5% biotinylated lipid were combined in the indicated amounts and the solvents evaporated. Water was added to yield a solution 30 mM in acyl chains. The lipid/water mixture was then sonicated for at least one hour. During sonication, the pH of the solution was maintained between 7 and 8 with NaOH and the temperature was maintained above the gel-liquid crystal phase transition point by the heat generated by sonication. The liposomes were transferred to a petri dish resting on a bed of wet ice and UV irradiated at 254 nm for at least one hour to polymerize. The paramagnetic polymerized liposomes were collected after passage through a 0.2 µ filter. The resulting paramagnetic polymerized liposomes were dark blue and exhibited absorption bands at 544 nm, 588 nm and 638 nm ($\lambda_{max}$). Gentle heating turned the paramagnetic polymerized liposomes red having absorption maxima at 498 nm and 538 nm. All paramagnetic polymerized liposomes used in this study were converted to the red form.

To form antibody conjugated paramagnetic polymerized liposomes, 2.3 µg avidin was combined with 14.9 µg biotinylated antibody in phosphate buffered saline in about 1:3 molar ratio and incubated at room temperature for 15 minutes. This solution was combined with 150 µL of the above formed paramagnetic polymerized liposomes, 5.6 mM in acyl chains, and incubated at 4° C. overnight to form the anti-cell adhesion molecule antibody-avidin conjugation to the biotinylated polymerized liposomes. FIG. 28 schematically shows the antibody-conjugated paramagnetic polymerized liposome (ACPL) formed as described above.

EXAMPLE IX

Attachment of the monoclonal antibodies to the biotinylated paramagnetic polymerized liposomes, as prepared in Example VIII, was confirmed using gel electrophoresis and immunodetection techniques.

For gel electrophoresis, samples were run on 0.65% agarose gels under non-denaturing conditions, running buffer 25 mM Tris, 190 mM glycine, pH 7.5. Gels were fixed in a solution of 45% methanol and 10% acetic acid for 15 minutes, rinsed overnight in water, incubated in 1% rabbit normal serum for 2 hours at room temperature, and incubated overnight at 4° C. with a 1:1000 dilution in PBS of alkaline phosphatase-conjugated antibodies against avidin (Sigma) or γ-immunoglobulin (Victor Laboratories, Burlingame, Calif.). After rinsing in several changes of PBS, gels were incubated at room temperature in the enzyme substrate, 5-bromo 4-chloro 3-indolyl phosphate 0.16 mg/ml and nitro blue tetrazolium 0.32 mg/ml (Sigma) in 0.1M NaCl, 0.1 M Tris, 50 mM $MgCl_2$, pH 9.5, until the gel was adequately developed. The reaction was stopped by rinsing in 1 mM EDTA. The paramagnetic polymerized liposomes contain a chromophore and were therefore visible without staining.

Gel electrophoresis, using anti-avidin alkaline phosphatase, in FIG. 29, showed in Lane 1 intense staining of 0.5 µg avidin, which, apparently at its isoelectric point, moved slowly from the loading well. Lane 2 showed a 5 µL sample of paramagnetic polymerized liposomes moved as a discrete band toward the positive pole. A solution of approximately 1:3 molar ratio of avidin, 4 µg, and unbiotinylated anti-CAM antibody, 26.25 µg, was incubated in a total volume of 60.5 µL PBS at 4° C. for 48 hours. A 3.2 µL aliquot of this solution was added to 16 μL of paramagnetic polymerized liposomes and incubated for approximately 1 week at 4° C. A 5 μL sample of paramagnetic polymerized liposomes pre-incubated with avidin and unbiotinylated anti-CAM antibody, as prepared above, showed, in Lane 3, avidin co-migrated with the liposome band, indicating the avidin was bound to the surface of the paramagnetic polymerized liposomes. No free avidin was detected near the well. Antibody-conjugated paramagnetic polymerized liposomes were prepared in the manner described above, except that biotinylated anti-CAM antibody was used, allowing conjugation of the antibody to the avidin-paramagnetic polymerized liposome complex to form antibody-conjugated paramagnetic polymerized liposomes. A 5 μL sample of the biotinylated anti-CAM antibody-conjugated polymerized liposomes showed, in Lane 4, no free avidin detected indicating that the avidin was bound to the paramagnetic polymerized liposomes. However, no avidin band appeared with the liposomes, suggesting that antibody conjugation to the particle surface sterically hindered binding of the anti-avidin alkaline phosphatase immunodetection antibody to the complex.

For immunodetection by anti-IgG alkaline phosphatase to assess antibody binding to the paramagnetic polymerized liposomes, paramagnetic polymerized liposome preparations and antibody/avidin incubations were performed as described above for the anti-avidin alkaline phosphatase immunodetection. FIG. 30 shows a 2.5 μg aliquot of biotinylated anti-CAM antibody moved as a distinct band in Lane 1 toward the negative pole. A 5 μL sample of paramagnetic polymerized liposome, as above, showed in Lane 2, movement toward the positive pole, being visible due to its intrinsic chromophore. A 5 μL sample of paramagnetic polymerized liposomes pre-incubated with avidin and unbiotinylated antibody, 2.2 μg total antibody, exhibited a free antibody band, in Lane 3, indicating that unbiotinylated antibody did not bind with the avidin-paramagnetic polymerized liposome complex. A 5 μL sample of paramagnetic polymerized liposomes pre-incubated with avidin and biotinylated antibody, 2.2 μg total antibody, in Lane 4, exhibited no detection of a free antibody band, demonstrating conjugation of the biotinylated antibody to the avidin-paramagnetic polymerized liposomes forming antibody-conjugated paramagnetic polymerized liposomes.

This Example shows that the antibody-conjugated paramagnetic polymerized liposome is functional in a competitive ELISA assay. Anti-ICAM-1 antibody-conjugated paramagnetic polymerized liposomes incubated on ELISA plates coated with soluble ICAM-1 demonstrated inhibition of free monoclonal anti-ICAM-1 antibody binding.

EXAMPLE X

Cell-binding assays using fluorescently-tagged antibody-conjugated paramagnetic polymerized liposomes were conducted to show that the anti-ICAM-1 antibody-conjugated paramagnetic polymerized liposomes could recognize antigens in vitro. Paramagnetic polymerized liposomes, as prepared in Example VIII, were coupled to Texas Red flurophore (Pierce, Rockford, Ill.). 200 μg Texas Red sulfonyl chloride in acetonitrile was added to 600 μl paramagnetic polymerized liposomes, 30 mM in acyl chain, in 0.1M sodium bicarbonate buffer, pH 9, and reacted at room temperature for 2 hours. The labeled paramagnetic polymerized liposomes were then purified by gel filtration (Sephadex G-25, Sigma, St. Louis, Mo.) using PBS as eluent. Fluorescent paramagnetic polymerized liposomes were then conjugated to anti-ICAM-1 antibodies as described in the prior example.

Figure 32:
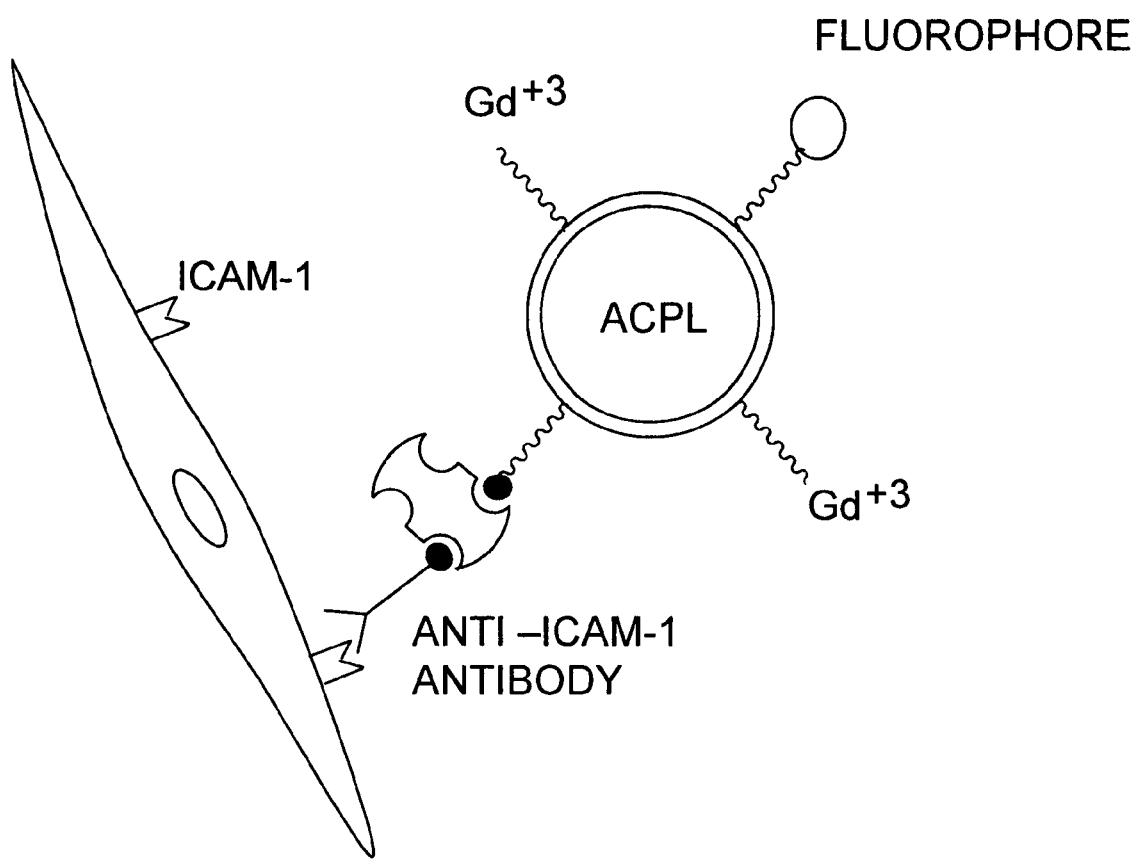
FIG. 32 shows schematically the cell binding shown in FIG. 31.

Endothelial cells, bEnd 3, were plated onto 100 mm plastic petri dishes and grown until confluent. Cells were stimulated with 1 μg/ml bacterial lipopolysaccharide about 24–48 hours prior to use to elicit expression of ICAM-1. Unstimulated cells constitutively expressing only low levels of adhesion molecules were used as controls. Media was aspirated from cells and the plates were rinsed with Hank's balanced salt solution for 30 minutes, washed three times with PBS and then divided in 1 $cm^2$ wells. The wells were pre-incubated with 0.5% bovine serum albumin in PBS for approximately 3 hours at room temperature following which aliquots of 50 μL each of 1:100 and 1:1000 dilutions of antibody-conjugated paramagnetic polymerized liposomes were added to cover the wells. Antibody-conjugated paramagnetic polymerized liposomes were incubated with the cells for 2 hours at room temperature and then washed two times for five minutes with 0.5% BSA-PBS and four times for five minutes with PBS. Using fluorescence microscopy, fluorescently tagged anti-ICAM-1 antibody-conjugated paramagnetic polymerized liposomes were seen bound to the cultured endothelial cells stimulated with bacterial lipopolysaccharide to elicit ICAM-1 expression, outlining the morphology of individual cell membranes, as shown in FIG. 31. This binding is shown schematically in FIG. 32. No binding of fluorescent antibody-conjugated paramagnetic polymerized liposomes to stimulated cells was observed when a non-specific anti-immunoglobulin antibody was substituted for anti-ICAM-1. Similarly, unstimulated cells that express only low levels of ICAM-1 did not bind anti-ICAM-1 fluorescent antibody-conjugated paramagnetic polymerized liposomes.

EXAMPLE XI

To show that antibody-conjugated paramagnetic polymerized liposomes could both successfully target endothelial CAMs in vivo and also provide substantial magnetic resonance image contrast enhancement, a well documented model of cerebral inflammation in mice was examined.

Experimental autoimmune encephalitis is an ascending encephalomyelitis characterized by an intense perivascular lympho-/monocytic inflammatory process in the central nervous system white matter, primarily the cerebellum, brain stem and spinal cord. This system is of clinical interest as an animal model for multiple sclerosis and the nature of the receptors involved in inflammatory cell trafficking in experimental autoimmune encephalitis have been well investigated. ICAM-1 expression on the experimental autoimmune encephalitis mouse brain microvasculature has been shown to be upregulated at the onset of clinical disease. The ICAM-1 receptor mediates the attachment of leukocytes to inflamed endothelium and is present on both activated leukocytes and stimulated endothelium of capillaries and venules throughout the central nervous system. Its expression is not limited to vessels involved by inflammatory infiltrates. Histologic studies have previously shown that the blood-brain barrier maintains integrity during the onset of disease and for 48 hours after paralysis is apparent. Prior magnetic resonance and fluorescence microscopy studies of liposome transit across the blood-brain barrier in acute experimental autoimmune encephalitis guinea pigs have shown that liposomes were unable to penetrate compromised blood-brain barrier and enter brain parenchyma. Therefore, we targeted the ICAM-1 receptor in the early phase of its upregulation in experimental autoimmune encephalitis, when expression of ICAM-1 is increased tenfold.

Fluorescently labeled anti-ICAM-1 antibody-conjugated paramagnetic polymerized liposomes were shown in vivo to bind to cerebellar vasculature of mice with grade 2 experimental autoimmune encephalitis by showing location of the particle as seen by high resolution magnetic resonance could be confirmed with fluorescence microscopy.

Experimental autoimmune encephalitis was induced in SJL/J mice according to a proteolipid protein immunization protocol. When clinical signs of grade 2 disease were apparent, tail paralysis and limb weakness, the fluorscent anti-ICAM-1 antibody-conjugated paramanetic polymerized liposomes, as prepared in the prior example, were injected via a tail vein, 10 $\mu$L/g representing 1.2 mg/kg Gd$^{+3}$ and 890 $\mu$g antibody/kg, and allowed to recirculate for 24 hours. Mice were then sacrificed and perfused with PBS. The brains were removed and cut in half sagitally, one half frozen for direct fluorscence microscope analysis of 10 $\mu$m thin sections and the other half fixed in 4% paraformaldehyde in PBS, pH7.4, and used for high resolution magnetic resonance imaging.

Figure 33:
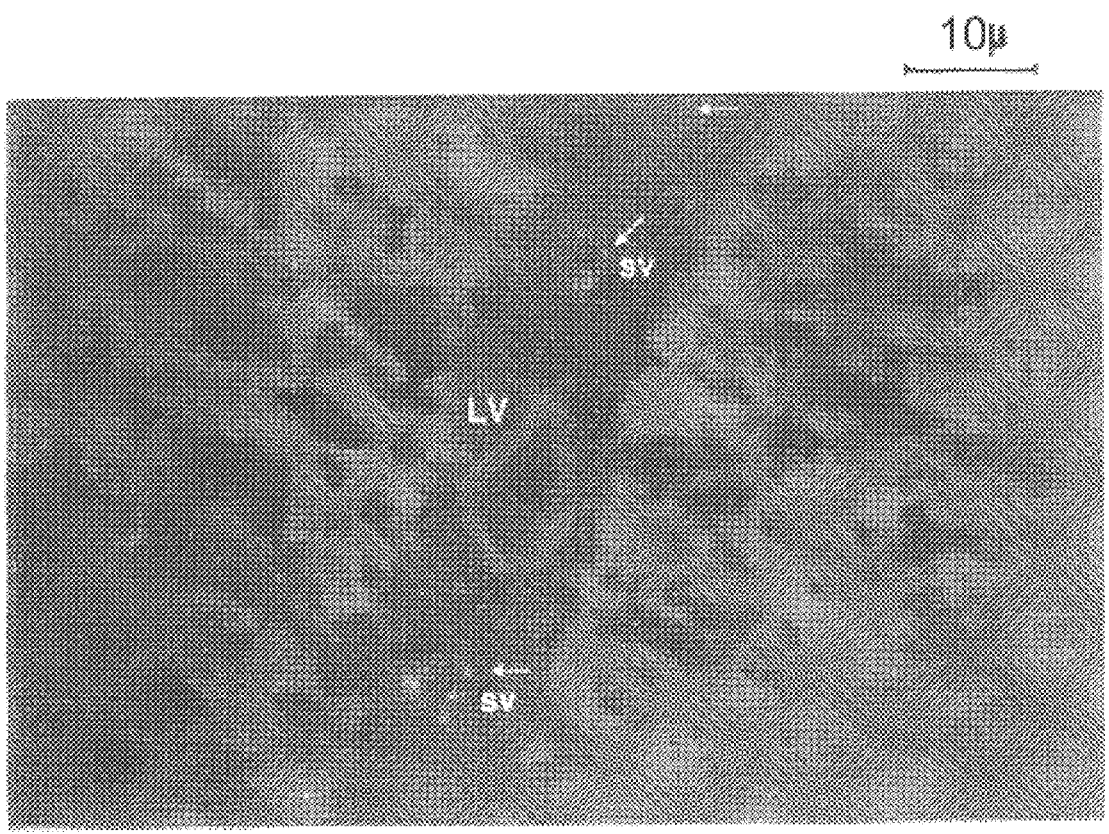
FIG. 33 is a fluorescence micrograph in color of mouse cerebellum showing anti-ICAM-1 antibody-conjugated polymerized liposomes bound to capillaries as described in Example XI.

In three separate tests, a total of seven diseased mice were injected with fluorescent anti-ICAM-1 antibody-conjugated paramagnetic polymerized liposomes and all were shown to be positive for the antibody conjugated-polymerized liposome binding to central nervous system vasculature by fluorescence microscopic analysis of cerebellum, brainstem and spinal cord. FIG. 33 is a typical fluorscence micrograph of mouse cerebellum counterstained with haematoxylin showing multiple vessels surrounded by an inflammatory infiltrate. Anti-ICAM-1 antibody-conjugated paramagnetic polymerized liposomes, indicated by arrows, are seen by fluorescence to be bound to small capillaries (SV), but not bound to large central arteriole (LV) which is seen to be negative for fluorescence. This is consistent with expression of ICAM-1 which is upregulated on endothelium of venules and capillaries, but not expressed on arterioles or larger vessels. We also noted fluorescent anti-ICAM-1 polymerized liposomes bound to microvessels that are not associated with inflammatory infiltrates, which is consistent with histological findings of ICAM-1 expression on both infiltrated and non-infiltrated vessels.

Six controls: three healthy animals injected with anti-ICAM-1 antibody-conjugated paramagnetic polymerized liposomes; two diseased animals administered antitrinitrophenol antibody-conjugated paramagnetic polymerized liposomes, and one diseased animal administered anti-V$\beta$11 T-cell receptor antibody-conjugated paramagnetic polymerized liposomes, targeted to an antigen not expressed in the SJL/J mouse, were all found by fluorescence microscopy to show no polymerized liposome binding.

EXAMPLE XII

Figure 34:
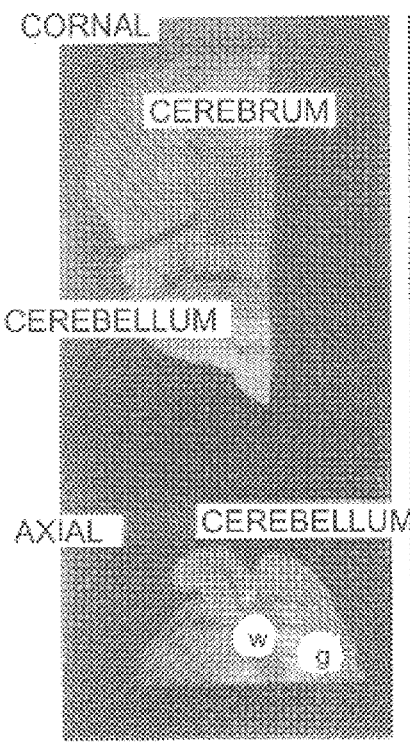
FIG. 34 is a magnetic resonance image of a brain slice of an experimental autoimmune encephalitis mouse without injection of polymerized liposomes as described in Example XII.
Figure 35:
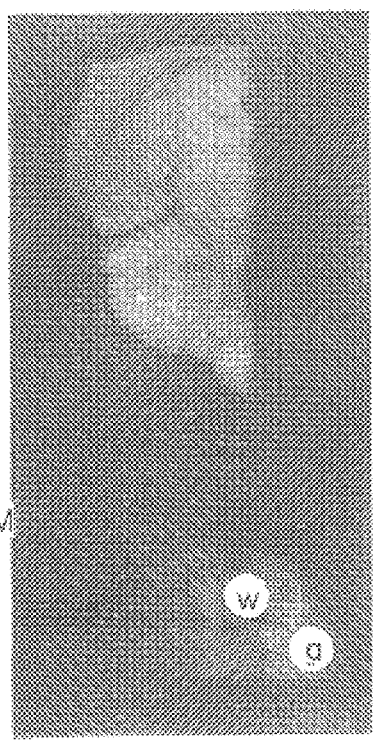
FIG. 35 is a magnetic resonance image of a brain slice of an experimental autoimmune encephalitis mouse injected with anti-ICAM-1 antibody-conjugated paramagnetic polymerized liposomes as described in Example XII.
Figure 36:
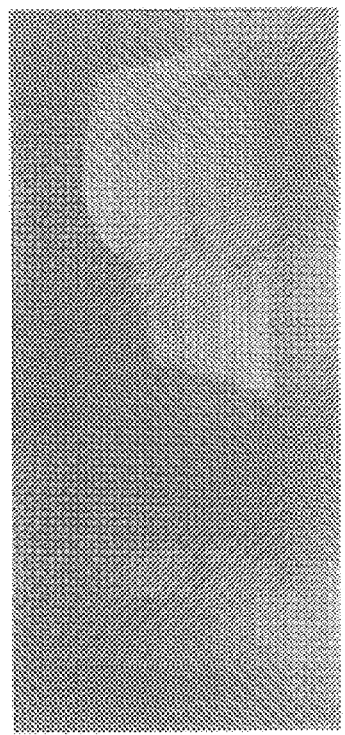
FIG. 36 is a magnetic resonance image of a brain slice of a healthy mouse injected with anti-ICAM-1 antibody-conjugated paramagnetic polymerized liposomes as described in Example XII.

High resolution magnetic resonance images were made of the complimentary half of two mouse brains from mice having grade 2 experimental autoimmune encephalitis used in the previous example containing anti-ICAM-1 antibody-conjugated paramagnetic polymerized liposomes. High resolution T1 and T2-weighted images of the intact half brains were obtained by using a 9.4T MR scanner (General Electric) using 3DFT spin echo pulse sequences. Parameters for T1-weighted images were TR 200 ms, TE 4 ms, 1 NEX, matrix 256×256×256, and a field of view of 1 cm, resulting in a voxel size of approximately 40 $\mu$m in each dimension. T1-weighted acquisitions times were approximately 7 hours per scan. T2-weighted parameters were TR 1000 ms, TE 20 ms, 8 NEX, matrix 256×256×256. T2-weighted scan times were approximately 12 hours. FIG. 34 shows a T2-weighted scan of an experimental autoimmune encephalitis mouse, without injection of polymerized liposomes, cerebrum (coronal) and cerebellum (axial) to define normal anatomy. FIG. 35 shows a representative slice from a T1-weighted scan of an autoimmune encephalitis mouse injected with anti-ICAM-1 antibody-conjugated paramagetic polymerized liposomes. Diffuse perivascular enhancement is seen throughout the brain, in the cerebellum and cerebrum, lending particularly significant contrast between the meagerly vascularized cerebellar white (W) and the highly vascular grey (g) matter. FIG. 36 shows a representative slice from a T1-weighted scan of a healthy mouse similarly injected with anti-ICAM-1 antibody-conjugated paramagnetic polymerized liposomes showed no enhancement.

Figure 37:
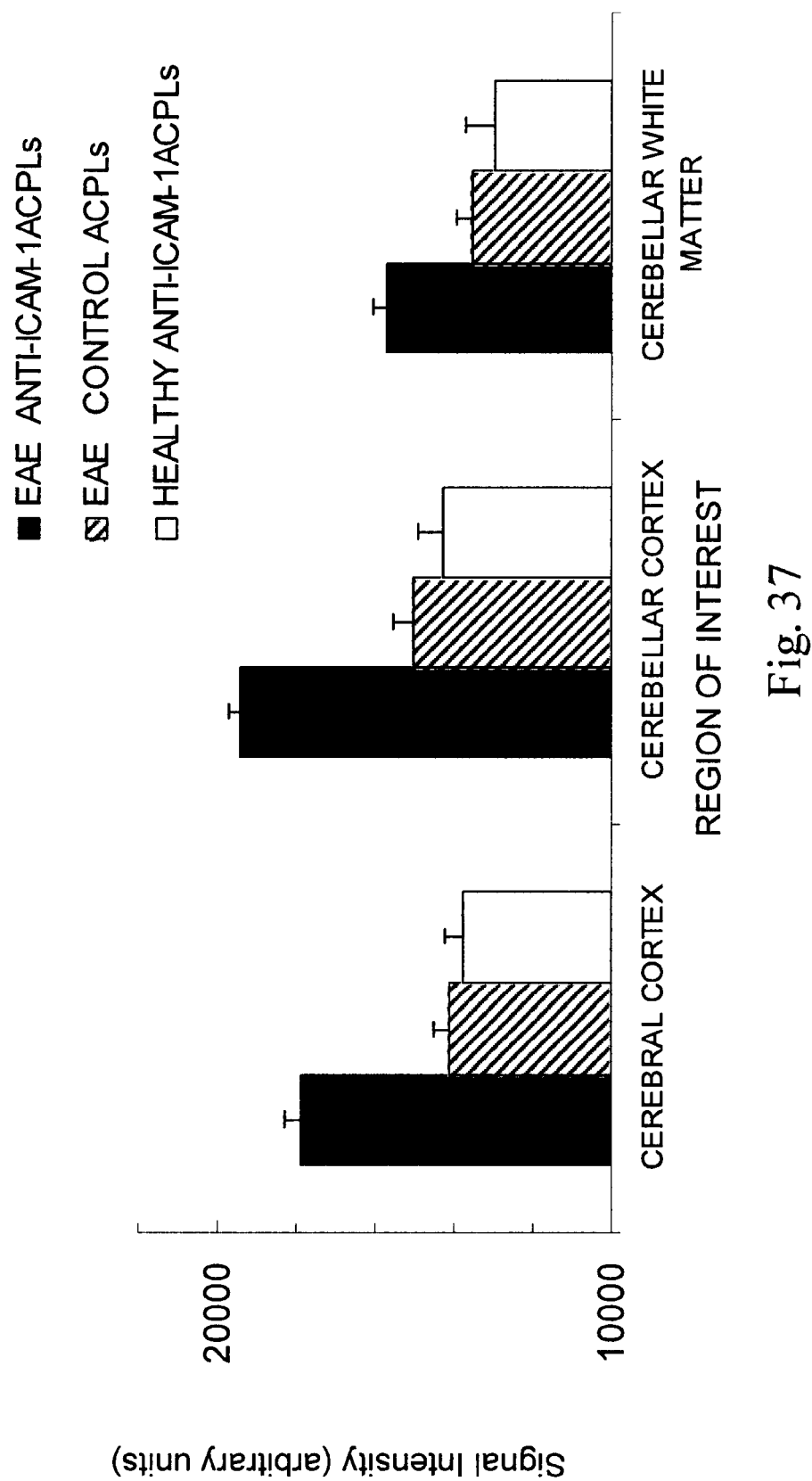
FIG. 37 is a bar chart showing magnetic resonance image intensity measurements as described in Example XII.

Signal intensity measurements were made using the image analysis program Voxel View/Ultra 2.2 (Vital Images, Inc., Fairfield, Iowa). For each mouse brain, three slices were chosen for analysis. For each slice, the signal intensity of cerebral gray, cerebellar gray, and cerebellar white matter was determined by manually drawing at least five large region-of-interest paths within each of these tissues. Signal intensity measurements from the three slices were averaged to give a mean signal intensity value for each tissue type, means weighted according to standard deviation of individual signal intensity values. The differences in tissue signal intensities between mouse brains were assessed using the two-tailed Stundent's t-test. The statistical significance level was set at $P<0.05$. The results are shown in FIG. 37. Compared to the controls, the magnetic resonance scans of the experimental autoimmune encephalytis infected mice injected with anti-ICAM-1 antibody-conjugated paramagnetic polymerized liposomes showed substantial increases in magnetic resonance signal intensity of about 32% in the cerebellar, 28% in the cerebral cortex and, to a lesser extent, about 18% in the cerebellar white matter. As a result of the enhanced gray matter signal, contrast between gray and white matter was improved. This was particularly pronounced in the cerebellum which was actively affected by experimental autoimmune encephalytis.

The above examples have demonstrated that antibody-conjugated paramagnetic polymerized liposomes can be delivered to cell adhesion molecules upregulated in disease. This provides a new target-specific magnetic resonance contrast enhancement agent for providing in vivo imaging studies of specific targeted physiological activies, such as, for example, endothelial antigens involved in numerous pathologies.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

What is claimed is:

1. A functional lipid having an active hydrophilic head group, said hydrophilic head group selected from the group consisting of a metal chelate or metal chelator, a liposome forming lipid, said liposome forming lipid comprising a hydrophobic tail group, said hydrophobic tail group having a polymerizable functional group, said hydrophilic head group and said liposome forming lipid being linked by a bifunctional linker portion.

2. A functional lipid according to claim 1 wherein said hydrophilic head group comprises a metal-diethylenetriamine pentaacetic acid chelate and said bifunctional linker portion is selected from the group consisting of bifunctional aliphatic compound and bifunctional aromatic compound.

3. A functional lipid according to claim 1 wherein said hydrophilic head group comprises a metal-diethylenetriamine pentaacetic acid chelate and said bifunctional linker portion is selected from the group consisting of polyethylene glycol, propylene glycol and polyglycine.

* * * * *